(12) United States Patent
Ruoslahti et al.

(10) Patent No.: US 6,576,239 B1
(45) Date of Patent: Jun. 10, 2003

(54) ANGIOGENIC HOMING MOLECULES AND CONJUGATES DERIVED THEREFROM

(75) Inventors: Erkki Ruoslahti, Rancho Santa Fe, CA (US); Renata Pasqualini, Solana Beach, CA (US)

(73) Assignee: The Burnham Institute, La Jolla, CA (US)

(*) Notice: Subject to any disclaimer, the term of this patent is extended or adjusted under 35 U.S.C. 154(b) by 0 days.

(21) Appl. No.: 08/926,914

(22) Filed: Sep. 10, 1997

Related U.S. Application Data

(60) Provisional application No. 60/060,947, filed on Sep. 10, 1996.

(51) Int. Cl.$^7$ ............................................... A61K 39/00
(52) U.S. Cl. ....................... 424/185.1; 424/1.57; 514/2; 514/8; 530/300; 530/324; 530/328
(58) Field of Search ............................ 424/1.57, 185.1; 514/2, 8; 530/300, 324, 328

(56) References Cited

U.S. PATENT DOCUMENTS

| | | | |
|---|---|---|---|
| 5,464,938 A | * 11/1995 | Smith et al. | |
| 5,536,814 A | 7/1996 | Ruoslahti et al. | ............ 530/329 |
| 5,622,699 A | 4/1997 | Ruoslahti et al. | ........... 424/93.6 |

FOREIGN PATENT DOCUMENTS

| | | | |
|---|---|---|---|
| EP | 0 135 277 | 3/1985 | |
| EP | 0 410 537 | 7/1990 | |
| EP | 0 639 584 | 2/1995 | |
| WO | 92/00091 | 1/1992 | |
| WO | 92/03461 | 3/1992 | |
| WO | 92/06191 | 4/1992 | |
| WO | 94 11003 A | 5/1994 | .......... A61K/31/56 |
| WO | 95/14714 | 6/1995 | |
| WO | 95 14714 A | 6/1995 | ........... C07K/14/75 |
| WO | 97 10507 A | 3/1997 | ......... G01N/33/567 |
| WO | 97/19954 | 6/1997 | |

OTHER PUBLICATIONS

Amoscuto et al. J. Immunol. 142:1245–1252, 1989.*
Amoscuto et al. Bioch. Biophys. Acta Abstract only, 1990.*
Chen et al. J. Immunol. 157:2593–2600, 1996.*
E. Koivunen et al., "Selection of peptides binding to the alphaV–betaI integrin form phage display library," *J. Biol. Chem.* (Microfilms) 268(27):20205–20210 (1993).
E. Koivunen et al., "Phage Libraries Displaying Cyclic Peptides with Different Ring Sizes: Ligand Specificities of the RGD–Directed Integrins," *Biotechnology*, 13(3):265–170 (1995).
B.M. Muller et al., "Pre–clinical therapy of human melanoma with morpholino–doxorubicin conjugated to a monoclonal antibody directed against an integrin on melanoma cells,"*Chemical Abstracts*, 115(21):222872 (1991).
Pasqualini and Ruoslahti, "Organ Targeting In Vivo Using Phage Display Peptide Libraries," *Nature*, 380:364–366 (1996).

Baillie et al., "Tumor Vasculature–A Potential Therapeutic Target" *British J. Cancer* 72:257–267 (1995).
R. Bicknell, "Vascular targeting and the inhibition of angiogenesis," *Annals of Oncology*, 5(Supp. 4): S45–S50 (1994).
Brooks et al., "Integrin $\alpha v \beta_3$ Antagonists Promote Tumor Regression by Inducing Apoptosis of Angiogenic Blood Vessels," *Cell*, 79:1157–1164 (1994).
Burioni et al., "Recombinant human Fab to glycoprotein D neutralizes infectivity and prevents cell–to–cell transmission of herpes simples viruses 1 and 2 in vitro," *Proc. Natl. Acad. Sci. USA*, 91:355–359 (1994).
Burrows and Thorpe, "Vascular Targeting–A New Approach to the Therapy of Solid Tumors" *Pharmac. Ther.* 64:155–174 (1994).
Cattani et al.; "Cloning and characterization of human recombinant antibody Fab fragments specific for types 1 and 2 herpes simplex virus," *Chemical Abstracts*, 123(11): Abstract 141201 (and Microbiologica, 18(2):135–142 (1995).
Dvorak et al., "Structure of Solid Tumors and Their Vasculature: Implications for Therapy with Monoclonal Antibodies" *Cancer Cell* 3:77–85 (1991).
J. Folkman, "Addressing tumor blood vessels," *Nature Biotechnology*, 15:510 (1997).
Friedlander et al., "Definition of Two Angiogenic Pathways by Distinct $\alpha_v$ integrins," *Science*, 270:1500–1502 (1995).
Furka et al., "General method for rapid synthesis of multicomponent peptide mixtures," *Intl. J. of Peptide and Protein Research*, 37(6):487–493 (1991).
Geier et al., "High–affinity urokinase receptor antagonists identified with bacteriophage peptide display," *Proc. Natl. Acad. Sci. USA*, 91:7129–7133 (1994).
Goodson et al., "High–affinity urokinase receptor antagonist identified with bacteriophage peptide display," *Proc. Nat. Acad. Sci. USA*, 91:7129–7133 (1994).
Goetz et al., "Lu–ECAM–1–Mediated Adhesion of Melanoma Cells to Endothelium Under Conditions of Flow" *Int. J. Cancer* 65:192–199 (1996).

(List continued on next page.)

Primary Examiner—Patrick J. Nolan
Assistant Examiner—Gerald R Ewoldt
(74) Attorney, Agent, or Firm—Campbell & Flores LLP

(57) ABSTRACT

The present invention provides tumor homing molecules, which selectively home to a tumor. The invention also provides methods of using a tumor homing molecule to target an agent such as a drug to a selected tumor or to identify the target molecule expressed by the tumor. The invention also provides methods of targeting a tumor containing angiogenic vasculature by contacting the tumor with a molecule that specifically binds an $\alpha_v$-containing integrin. The invention further provides molecules that can selectively home to angiogenic vasculature. In addition, the invention provides a target molecule, which is specifically bound by a tumor homing molecule and is expressed by angiogenic vasculature. The invention also provides antibodies that bind to the target molecule and peptidomimetics that competitively inhibit binding of a ligand to the target molecule.

33 Claims, 5 Drawing Sheets

OTHER PUBLICATIONS

Hammes et al., "Subcutaneous injection of a cyclic peptide antagonist of vitronectin receptor–type integrins inhibits retinal neovascularization," *Nature Medicine*, 2(5):529–533 (1996).

D. Hanahan, "Signaling Vascular Morphogenesis and Maintenance," *Science*, 277:48–50 (1997).

Hart et al., "Cell Binding and Internalization by Filamentous Phage Displaying a Cyclic Arg–Gly–Asp–containing Peptide," *J. of Biol. Chem.*, 269(17):12468–12474 (1994).

Healy et al., "Peptide Ligands for Integrin $\alpha_v\beta_3$ Selected from Random Phage Display Libraries," *Biochem.*, 34:3948–3955 (1995).

Hornik and Hadas, "Self–encoded, highly condensed solid phose–supported peptide library for identification of ligand-specific peptides," *Chem. Abstracts*, 121(7): Abstract 77731p (1994), React. Polym. 22(3):213–220 (1994).

Huang et al., "Tumor Infarction in Mice by Antibody–Directed Targeting of Tissue Factor to Tumor Vasculature" *Science* 275:547–550 (1997).

R. Kerbel, "Inhibition of Tumor Angiogenesis as a Strategy to Circumvent Acquired Resistance to Anti–Cancer Therapeutic Agents," *BioEssays*, 13(1):31–36 (1991).

D. Lappi, "Tumor Targeting Through Fibroblast Growth Factor Receptors" *Cancer Biology* 6:279–288 (1995).

Martiny–Baron and Marmé, "VEGF–mediated Tumor Angiogenesis: A New Target for Cancer Therapy" *Current Biology* 6:675–680 (1995).

Miner et al., "Clonal Drift of Cell Surface, Melanogenic, and Experimental Metastatic Properties of in vivo–selected, Brain Meninges–colonizing Murine B16 Melanoma" *Cancer Research* 42:4631–4638 (1982).

Mitjans et al., "An anti–$\alpha$v–integrin antibody that blocks integrin function inhibits the development of a human melanoma in nude mice," *J. Cell Sci.*, 108:2825–2838 (1995).

Nagy et al., "Cytotoxic analogs of luteinizing hormone–releasing hormone containing doxorubicin or 2–pyrrolino-doxorubicin, a derivative 500–1000 times more potent," *Proc. Natl. Acad. Sci. USA*, 93:7269–7273 (1996).

Pasqualini et al., "$\alpha$v Integrins as receptors for tumor targeting by circulating ligands," *Nature Biotechnolgy*, 15:542–546 (1997).

Pasqualini and Ruoslahti, "Organ Targeting in vivo Using Phage Dispay Peptide Libraries" *Nature* 380:364–366 (1996).

Pauli et al., "Consequences of angiogenesis for tumor progression, metastasis and cancer therapy," *Anti–Cancer Drugs*, 6:3–18 (1995).

Rak et al., "Consequences of angiogenesis for tumor progression, metastasis and cancer therapy," *Anti–Cancer Drugs*, 6:3–18 (1995).

E. Ruoslahti, "RGD and other recognition sequences for integrins," *Annu. Rev. Cell Dev. Biol.*, 12:697–715 (1996).

Tjoeng et al., "Multiple peptide synthesis using a single support (MPS3)," *Intl. J. of Peptide and Protein Research*, 35(2):141–146 (1990).

Trail et al., "Cure of Xenografted Human Carcinomas by BR96–Doxorubicin Immunoconjugates," *Science*, 261:212–215 (1993).

Zhu et al., "Mediation of Lung Metastasis of Murine Melanomas by a Lung–specific Endothelial Cell Adhesion Molecule," *Proc. Natl. Acad. Sci. USA* 88:9568–9572 (1991).

\* cited by examiner

SEQUENCE LISTING (1) GENERAL INFORMATION:

(iii) NUMBER OF SEQUENCES: 199

(2) INFORMATION FOR SEQ ID NO:1:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:1:

Cys Asp Cys Arg Gly Asp Cys Phe Cys
1               5

(2) INFORMATION FOR SEQ ID NO:2:

(i) SEQUENCE CHARACTERISTICS:
        (A) LENGTH: 13 amino acids
        (B) TYPE: amino acid
        (D) TOPOLOGY: both (ii) MOLECULE TYPE: peptide (xi) SEQUENCE DESCRIPTION: SEQ ID NO:2:

Cys Gly Arg Glu Cys Pro Arg Leu Cys Gln Ser Ser Cys
1               5                   10

(2) INFORMATION FOR SEQ ID NO:3:

(i) SEQUENCE CHARACTERISTICS:
        (A) LENGTH: 13 amino acids
        (B) TYPE: amino acid
        (D) TOPOLOGY: both (ii) MOLECULE TYPE: peptide (xi) SEQUENCE DESCRIPTION: SEQ ID NO:3:

Cys Asn Gly Arg Cys Val Ser Gly Cys Ala Gly Arg Cys
1               5                   10

(2) INFORMATION FOR SEQ ID NO:4:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:4:

Cys Leu Ser Gly Ser Leu Ser Cys
1               5

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:5:

```
Cys Gly Ser Leu Val Arg Cys
1               5

(2) INFORMATION FOR SEQ ID NO:6:

(i) SEQUENCE CHARACTERISTICS:
         (A) LENGTH: 6 amino acids
         (B) TYPE: amino acid
         (D) TOPOLOGY: both (ii) MOLECULE TYPE: peptide (xi) SEQUENCE DESCRIPTION: SEQ ID NO:6:

Asn Gly Arg Ala His Ala
1               5

(2) INFORMATION FOR SEQ ID NO:7:

(i) SEQUENCE CHARACTERISTICS:
         (A) LENGTH: 9 amino acids
         (B) TYPE: amino acid
         (D) TOPOLOGY: both (ii) MOLECULE TYPE: peptide (xi) SEQUENCE DESCRIPTION: SEQ ID NO:7:

Cys Val Leu Asn Gly Arg Met Glu Cys
1               5

(2) INFORMATION FOR SEQ ID NO:8:

(i) SEQUENCE CHARACTERISTICS:
         (A) LENGTH: 5 amino acids
         (B) TYPE: amino acid
         (D) TOPOLOGY: both (ii) MOLECULE TYPE: peptide (xi) SEQUENCE DESCRIPTION: SEQ ID NO:8:

Cys Asn Gly Arg Cys
1               5

(2) INFORMATION FOR SEQ ID NO:9:

(i) SEQUENCE CHARACTERISTICS:
         (A) LENGTH: 7 amino acids
         (B) TYPE: amino acid
         (D) TOPOLOGY: both (ii) MOLECULE TYPE: peptide (xi) SEQUENCE DESCRIPTION: SEQ ID NO:9:

Cys Xaa Xaa Xaa Xaa Xaa Cys
1               5

(2) INFORMATION FOR SEQ ID NO:10:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:10:

Cys Xaa Xaa Xaa Xaa Xaa Xaa Cys
1               5
```

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:11:

Cys Xaa Xaa Xaa Xaa Xaa Xaa Xaa Cys
1               5

(2) INFORMATION FOR SEQ ID NO:12:

(i) SEQUENCE CHARACTERISTICS:
        (A) LENGTH: 13 amino acids
        (B) TYPE: amino acid
        (D) TOPOLOGY: both (ii) MOLECULE TYPE: peptide (xi) SEQUENCE DESCRIPTION: SEQ ID NO:12:

Cys Xaa Xaa Xaa Cys Xaa Xaa Xaa Cys Xaa Xaa Xaa Cys
1               5                  10

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:13:

Cys Xaa Xaa Xaa Asn Gly Arg Xaa Xaa
1               5

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:14:

Cys Xaa Xaa Cys Asn Gly Arg Cys Xaa
1               5

(2) INFORMATION FOR SEQ ID NO:15:

(i) SEQUENCE CHARACTERISTICS:
        (A) LENGTH: 12 amino acids
        (B) TYPE: amino acid
        (D) TOPOLOGY: both (ii) MOLECULE TYPE: peptide (xi) SEQUENCE DESCRIPTION: SEQ ID NO:15:

Cys Asn Lys Thr Asp Gly Asp Glu Gly Val Thr Cys
1               5                  10

(2) INFORMATION FOR SEQ ID NO:16:

(i) SEQUENCE CHARACTERISTICS:
        (A) LENGTH: 11 amino acids

```
            (B) TYPE: amino acid
            (D) TOPOLOGY: both (ii) MOLECULE TYPE: peptide (xi) SEQUENCE DESCRIPTION: SEQ ID NO:16:

Ala Cys Asp Cys Arg Gly Asp Cys Phe Cys Gly
1               5                  10

(2) INFORMATION FOR SEQ ID NO:17:

(i) SEQUENCE CHARACTERISTICS:
            (A) LENGTH: 6 amino acids
            (B) TYPE: amino acid
            (D) TOPOLOGY: both (ii) MOLECULE TYPE: peptide (xi) SEQUENCE DESCRIPTION: SEQ ID NO:17:

Gly Arg Gly Glu Ser Pro
1               5

(2) INFORMATION FOR SEQ ID NO:18:

(i) SEQUENCE CHARACTERISTICS:
            (A) LENGTH: 6 amino acids
            (B) TYPE: amino acid
            (D) TOPOLOGY: both (ii) MOLECULE TYPE: peptide (xi) SEQUENCE DESCRIPTION: SEQ ID NO:18:

Trp Gly Thr Gly Leu Cys
1               5

(2) INFORMATION FOR SEQ ID NO:19:

(i) SEQUENCE CHARACTERISTICS:
            (A) LENGTH: 13 amino acids
            (B) TYPE: amino acid
            (D) TOPOLOGY: both (ii) MOLECULE TYPE: peptide (xi) SEQUENCE DESCRIPTION: SEQ ID NO:19:

Gly Ala Cys Val Phe Ser Ile Ala His Glu Cys Gly Ala
1               5                  10

(2) INFORMATION FOR SEQ ID NO:20:

(i) SEQUENCE CHARACTERISTICS:
            (A) LENGTH: 13 amino acids
            (B) TYPE: amino acid
            (D) TOPOLOGY: both (ii) MOLECULE TYPE: peptide (xi) SEQUENCE DESCRIPTION: SEQ ID NO:20:

Cys Gly Glu Ala Cys Gly Gly Gln Cys Ala Leu Pro Cys
1               5                  10

(2) INFORMATION FOR SEQ ID NO:21:

(i) SEQUENCE CHARACTERISTICS:
            (A) LENGTH: 9 amino acids
            (B) TYPE: amino acid
            (D) TOPOLOGY: both (ii) MOLECULE TYPE: peptide
```

(xi) SEQUENCE DESCRIPTION: SEQ ID NO:21:

Ile Trp Ser Gly Tyr Gly Val Tyr Trp
1               5

(2) INFORMATION FOR SEQ ID NO:22:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:22:

Pro Ser Cys Ala Tyr Met Cys Ile Thr
1               5

(2) INFORMATION FOR SEQ ID NO:23:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:23:

Trp Glu Ser Leu Tyr Phe Pro Arg Glu
1               5

(2) INFORMATION FOR SEQ ID NO:24:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:24:

Ser Lys Val Leu Tyr Tyr Asn Trp Glu
1               5

(2) INFORMATION FOR SEQ ID NO:25:

(i) SEQUENCE CHARACTERISTICS:
            (A) LENGTH: 13 amino acids
            (B) TYPE: amino acid
            (D) TOPOLOGY: both (ii) MOLECULE TYPE: peptide (xi) SEQUENCE DESCRIPTION: SEQ ID NO:25:

Cys Gly Leu Met Cys Gln Gly Ala Cys Phe Asp Val Cys
1               5                   10

(2) INFORMATION FOR SEQ ID NO:26:

(i) SEQUENCE CHARACTERISTICS:
            (A) LENGTH: 13 amino acids
            (B) TYPE: amino acid
            (D) TOPOLOGY: both (ii) MOLECULE TYPE: peptide (xi) SEQUENCE DESCRIPTION: SEQ ID NO:26:

Cys Glu Arg Ala Cys Arg Asn Leu Cys Arg Glu Gly Cys

```
1               5                    10
```

(2) INFORMATION FOR SEQ ID NO:27:

(i) SEQUENCE CHARACTERISTICS:
        (A) LENGTH: 13 amino acids
        (B) TYPE: amino acid
        (D) TOPOLOGY: both (ii) MOLECULE TYPE: peptide (xi) SEQUENCE DESCRIPTION: SEQ ID NO:27:

```
Cys Pro Arg Gly Cys Leu Ala Val Cys Val Ser Gln Cys
1               5                   10
```

(2) INFORMATION FOR SEQ ID NO:28:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:28:

```
Cys Lys Val Cys Asn Gly Arg Cys Cys Gly
1               5                   10
```

(2) INFORMATION FOR SEQ ID NO:29:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:29:

```
Cys Glu Met Cys Asn Gly Arg Cys Met Gly
1               5                   10
```

(2) INFORMATION FOR SEQ ID NO:30:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:30:

```
Cys Pro Leu Cys Asn Gly Arg Cys Ala Leu
1               5                   10
```

(2) INFORMATION FOR SEQ ID NO:31:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:31:

```
Cys Pro Thr Cys Asn Gly Arg Cys Val Arg
1               5                   10
```

(2) INFORMATION FOR SEQ ID NO:32:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:32:

Cys Gly Val Cys Asn Gly Arg Cys Gly Leu
1               5                   10

(2) INFORMATION FOR SEQ ID NO:33:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:33:

Cys Glu Gln Cys Asn Gly Arg Cys Gly Gln
1               5                   10

(2) INFORMATION FOR SEQ ID NO:34:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:34:

Cys Arg Asn Cys Asn Gly Arg Cys Glu Gly
1               5                   10

(2) INFORMATION FOR SEQ ID NO:35:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:35:

Cys Val Leu Cys Asn Gly Arg Cys Trp Ser
1               5                   10

(2) INFORMATION FOR SEQ ID NO:36:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:36:

Cys Val Thr Cys Asn Gly Arg Cys Arg Val
1               5                   10

(2) INFORMATION FOR SEQ ID NO:37:

(i) SEQUENCE CHARACTERISTICS:
            (A) LENGTH: 10 amino acids
            (B) TYPE: amino acid (D) TOPOLOGY: both (ii) MOLECULE TYPE: peptide (xi) SEQUENCE DESCRIPTION: SEQ ID NO:37:

Cys Thr Glu Cys Asn Gly Arg Cys Gln Leu
1               5                   10

(2) INFORMATION FOR SEQ ID NO:38:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:38:

Cys Arg Thr Cys Asn Gly Arg Cys Leu Glu
1               5                   10

(2) INFORMATION FOR SEQ ID NO:39:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:39:

Cys Glu Thr Cys Asn Gly Arg Cys Val Gly
1               5                   10

(2) INFORMATION FOR SEQ ID NO:40:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:40:

Cys Ala Val Cys Asn Gly Arg Cys Gly Phe
1               5                   10

(2) INFORMATION FOR SEQ ID NO:41:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:41:

Cys Arg Asp Leu Asn Gly Arg Lys Val Met
1               5                   10

(2) INFORMATION FOR SEQ ID NO:42:

(i) SEQUENCE CHARACTERISTICS:
        (A) LENGTH: 10 amino acids
        (B) TYPE: amino acid
        (D) TOPOLOGY: both (ii) MOLECULE TYPE: peptide

```
   (xi) SEQUENCE DESCRIPTION: SEQ ID NO:42:

Cys Ser Cys Cys Asn Gly Arg Cys Gly Asp
1               5                   10

(2) INFORMATION FOR SEQ ID NO:43:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:43:

Cys Trp Gly Cys Asn Gly Arg Cys Arg Met
1               5                   10

(2) INFORMATION FOR SEQ ID NO:44:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:44:

Cys Pro Leu Cys Asn Gly Arg Cys Ala Arg
1               5                   10

(2) INFORMATION FOR SEQ ID NO:45:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:45:

Cys Lys Ser Cys Asn Gly Arg Cys Leu Ala
1               5                   10

(2) INFORMATION FOR SEQ ID NO:46:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:46:

Cys Val Pro Cys Asn Gly Arg Cys His Glu
1               5                   10

(2) INFORMATION FOR SEQ ID NO:47:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:47:

Cys Gln Ser Cys Asn Gly Arg Cys Val Arg
1               5                   10
```

(2) INFORMATION FOR SEQ ID NO:48:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:48:

```
Cys Arg Thr Cys Asn Gly Arg Cys Gln Val
1               5                   10
```

(2) INFORMATION FOR SEQ ID NO:49:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:49:

```
Cys Val Gln Cys Asn Gly Arg Cys Ala Leu
1               5                   10
```

(2) INFORMATION FOR SEQ ID NO:50:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:50:

```
Cys Arg Cys Cys Asn Gly Arg Cys Ser Pro
1               5                   10
```

(2) INFORMATION FOR SEQ ID NO:51:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:51:

```
Cys Ala Ser Asn Asn Gly Arg Val Val Leu
1               5                   10
```

(2) INFORMATION FOR SEQ ID NO:52:

(i) SEQUENCE CHARACTERISTICS:
        (A) LENGTH: 10 amino acids
        (B) TYPE: amino acid
        (D) TOPOLOGY: both (ii) MOLECULE TYPE: peptide (xi) SEQUENCE DESCRIPTION: SEQ ID NO:52:

```
Cys Gly Arg Cys Asn Gly Arg Cys Leu Leu
1               5                   10
```

(2) INFORMATION FOR SEQ ID NO:53:

```
        (i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:53:

Cys Trp Leu Cys Asn Gly Arg Cys Gly Arg
1               5                   10

(2) INFORMATION FOR SEQ ID NO:54:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:54:

Cys Ser Lys Cys Asn Gly Arg Cys Gly His
1               5                   10

(2) INFORMATION FOR SEQ ID NO:55:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:55:

Cys Val Trp Cys Asn Gly Arg Cys Gly Leu
1               5                   10

(2) INFORMATION FOR SEQ ID NO:56:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:56:

Cys Ile Arg Cys Asn Gly Arg Cys Ser Val
1               5                   10

(2) INFORMATION FOR SEQ ID NO:57:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:57:

Cys Gly Glu Cys Asn Gly Arg Cys Val Glu
1               5                   10

(2) INFORMATION FOR SEQ ID NO:58:

(i) SEQUENCE CHARACTERISTICS:
            (A) LENGTH: 10 amino acids
            (B) TYPE: amino acid
            (D) TOPOLOGY: both
```

(ii) MOLECULE TYPE: peptide (xi) SEQUENCE DESCRIPTION: SEQ ID NO:58:

Cys Glu Gly Val Asn Gly Arg Arg Leu Arg
1               5                   10

(2) INFORMATION FOR SEQ ID NO:59:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:59:

Cys Leu Ser Cys Asn Gly Arg Cys Pro Ser
1               5                   10

(2) INFORMATION FOR SEQ ID NO:60:

(i) SEQUENCE CHARACTERISTICS:
            (A) LENGTH: 10 amino acids
            (B) TYPE: amino acid
            (D) TOPOLOGY: both (ii) MOLECULE TYPE: peptide (xi) SEQUENCE DESCRIPTION: SEQ ID NO:60:

Cys Glu Val Cys Asn Gly Arg Cys Ala Leu
1               5                   10

(2) INFORMATION FOR SEQ ID NO:61:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:61:

Gly Arg Ser Gln Met Gln Ile
1               5

(2) INFORMATION FOR SEQ ID NO:62:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:62:

His His Thr Arg Phe Val Ser
1               5

(2) INFORMATION FOR SEQ ID NO:63:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:63:

```
Ser Lys Gly Leu Arg His Arg
1               5
```

(2) INFORMATION FOR SEQ ID NO:64:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:64:

```
Val Ala Ser Val Ser Val Ala
1               5
```

(2) INFORMATION FOR SEQ ID NO:65:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:65:

```
Trp Arg Val Leu Ala Ala Phe
1               5
```

(2) INFORMATION FOR SEQ ID NO:66:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:66:

```
Lys Met Gly Pro Lys Val Trp
1               5
```

(2) INFORMATION FOR SEQ ID NO:67:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:67:

```
Ile Phe Ser Gly Ser Arg Glu
1               5
```

(2) INFORMATION FOR SEQ ID NO:68:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:68:

```
Ser Pro Gly Ser Trp Thr Trp
1               5
```

(2) INFORMATION FOR SEQ ID NO:69:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:69:

Asn Pro Arg Trp Phe Trp Asp
1               5

(2) INFORMATION FOR SEQ ID NO:70:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:70:

Gly Arg Trp Tyr Lys Trp Ala
1               5

(2) INFORMATION FOR SEQ ID NO:71:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:71:

Ile Lys Ala Arg Ala Ser Pro
1               5

(2) INFORMATION FOR SEQ ID NO:72:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:72:

Ser Gly Trp Cys Tyr Arg Cys
1               5

(2) INFORMATION FOR SEQ ID NO:73:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:73:

Ala Leu Val Gly Leu Met Arg
1               5

(2) INFORMATION FOR SEQ ID NO:74:

(i) SEQUENCE CHARACTERISTICS:

(A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:74:

Leu Trp Ala Glu Met Thr Gly
1               5

(2) INFORMATION FOR SEQ ID NO:75:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:75:

Cys Trp Ser Gly Val Asp Cys
1               5

(2) INFORMATION FOR SEQ ID NO:76:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:76:

Asp Thr Leu Arg Leu Arg Ile
1               5

(2) INFORMATION FOR SEQ ID NO:77:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:77:

Ser Lys Ser Ser Gly Val Ser
1               5

(2) INFORMATION FOR SEQ ID NO:78:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:78:

Ile Val Ala Asp Tyr Gln Arg
1               5

(2) INFORMATION FOR SEQ ID NO:79:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:79:

Val Trp Arg Thr Gly His Leu
1               5

(2) INFORMATION FOR SEQ ID NO:80:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:80:

Val Val Asp Arg Phe Pro Asp
1               5

(2) INFORMATION FOR SEQ ID NO:81:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:81:

Leu Ser Met Phe Thr Arg Pro
1               5

(2) INFORMATION FOR SEQ ID NO:82:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:82:

Gly Leu Pro Val Lys Trp Ser
1               5

(2) INFORMATION FOR SEQ ID NO:83:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:83:

Ile Met Tyr Pro Gly Trp Leu
1               5

(2) INFORMATION FOR SEQ ID NO:84:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:84:

```
Cys Val Met Val Arg Asp Gly Asp Cys
1               5

(2) INFORMATION FOR SEQ ID NO:85:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:85:

Cys Val Arg Ile Arg Pro Cys
1               5

(2) INFORMATION FOR SEQ ID NO:86:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:86:

Cys Gln Leu Ala Ala Val Cys
1               5

(2) INFORMATION FOR SEQ ID NO:87:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:87:

Cys Gly Val Gly Ser Ser Cys
1               5

(2) INFORMATION FOR SEQ ID NO:88:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:88:

Cys Val Ser Gly Pro Arg Cys
1               5

(2) INFORMATION FOR SEQ ID NO:89:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:89:

Cys Gly Leu Ser Asp Ser Cys
1               5
```

(2) INFORMATION FOR SEQ ID NO:90:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:90:

Cys Gly Glu Gly His Pro Cys
1               5

(2) INFORMATION FOR SEQ ID NO:91:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:91:

Cys Tyr Thr Ala Asp Pro Cys
1               5

(2) INFORMATION FOR SEQ ID NO:92:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:92:

Cys Glu Leu Ser Leu Ile Ser Lys Cys
1               5

(2) INFORMATION FOR SEQ ID NO:93:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:93:

Cys Pro Glu His Arg Ser Leu Val Cys
1               5

(2) INFORMATION FOR SEQ ID NO:94:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:94:

Cys Leu Val Val His Glu Ala Ala Cys
1               5

(2) INFORMATION FOR SEQ ID NO:95:

(i) SEQUENCE CHARACTERISTICS:
        (A) LENGTH: 7 amino acids

```
            (B) TYPE: amino acid
            (D) TOPOLOGY: both (ii) MOLECULE TYPE: peptide (xi) SEQUENCE DESCRIPTION: SEQ ID NO:95:

Cys Tyr Val Glu Leu His Cys
1               5

(2) INFORMATION FOR SEQ ID NO:96:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:96:

Cys Trp Arg Lys Phe Tyr Cys
1               5

(2) INFORMATION FOR SEQ ID NO:97:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:97:

Cys Phe Trp Pro Asn Arg Cys
1               5

(2) INFORMATION FOR SEQ ID NO:98:

(i) SEQUENCE CHARACTERISTICS:
            (A) LENGTH: 8 amino acids
            (B) TYPE: amino acid
            (D) TOPOLOGY: both (ii) MOLECULE TYPE: peptide (xi) SEQUENCE DESCRIPTION: SEQ ID NO:98:

Cys Tyr Ser Tyr Phe Leu Ala Cys
1               5

(2) INFORMATION FOR SEQ ID NO:99:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:99:

Cys Pro Arg Gly Ser Arg Cys
1               5

(2) INFORMATION FOR SEQ ID NO:100:

(i) SEQUENCE CHARACTERISTICS:
            (A) LENGTH: 7 amino acids
            (B) TYPE: amino acid
            (D) TOPOLOGY: both (ii) MOLECULE TYPE: peptide
```

(xi) SEQUENCE DESCRIPTION: SEQ ID NO:100:

Cys Arg Leu Gly Ile Ala Cys
1               5

(2) INFORMATION FOR SEQ ID NO:101:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:101:

Cys Asp Asp Ser Trp Lys Cys
1               5

(2) INFORMATION FOR SEQ ID NO:102:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:102:

Cys Ala Gln Leu Leu Gln Val Ser Cys
1               5

(2) INFORMATION FOR SEQ ID NO:103:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:103:

Cys Tyr Pro Ala Asp Pro Cys
1               5

(2) INFORMATION FOR SEQ ID NO:104:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:104:

Cys Lys Ala Leu Ser Gln Ala Cys
1               5

(2) INFORMATION FOR SEQ ID NO:105:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:105:

Cys Thr Asp Tyr Val Arg Cys 1               5

(2) INFORMATION FOR SEQ ID NO:106:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:106:

Cys Gly Glu Thr Met Arg Cys
1               5

(2) INFORMATION FOR SEQ ID NO:107:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:107:

Gly Ile Cys Lys Asp Asp Trp Cys Gln
1               5

(2) INFORMATION FOR SEQ ID NO:108:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:108:

Thr Ser Cys Asp Pro Ser Leu Cys Glu
1               5

(2) INFORMATION FOR SEQ ID NO:109:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:109:

Lys Gly Cys Gly Thr Arg Gln Cys Trp
1               5

(2) INFORMATION FOR SEQ ID NO:110:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:110:

Tyr Arg Cys Arg Glu Val Leu Cys Gln
1               5

(2) INFORMATION FOR SEQ ID NO:111:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:111:

Cys Trp Gly Thr Gly Leu Cys
1               5

(2) INFORMATION FOR SEQ ID NO:112:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:112:

Trp Ser Cys Ala Asp Arg Thr Cys Met
1               5

(2) INFORMATION FOR SEQ ID NO:113:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:113:

Ala Gly Cys Arg Leu Lys Ser Cys Ala
1               5

(2) INFORMATION FOR SEQ ID NO:114:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:114:

Ser Arg Cys Lys Thr Gly Leu Cys Gln
1               5

(2) INFORMATION FOR SEQ ID NO:115:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:115:

Pro Ile Cys Glu Val Ser Arg Cys Trp
1               5

(2) INFORMATION FOR SEQ ID NO:116:

(i) SEQUENCE CHARACTERISTICS:
            (A) LENGTH: 9 amino acids
            (B) TYPE: amino acid (D) TOPOLOGY: both (ii) MOLECULE TYPE: peptide (xi) SEQUENCE DESCRIPTION: SEQ ID NO:116:

Trp Thr Cys Arg Ala Ser Trp Cys Ser
1               5

(2) INFORMATION FOR SEQ ID NO:117:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:117:

Gly Arg Cys Leu Leu Met Gln Cys Arg
1               5

(2) INFORMATION FOR SEQ ID NO:118:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:118:

Thr Glu Cys Asp Met Ser Arg Cys Met
1               5

(2) INFORMATION FOR SEQ ID NO:119:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:119:

Ala Arg Cys Arg Val Asp Pro Cys Val
1               5

(2) INFORMATION FOR SEQ ID NO:120:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:120:

Cys Ile Glu Gly Val Leu Gly Gly Cys
1               5

(2) INFORMATION FOR SEQ ID NO:121:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:121:

Cys Ser Val Ala Asn Ser Cys
1               5

(2) INFORMATION FOR SEQ ID NO:122:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:122:

Cys Ser Ser Thr Met Arg Cys
1               5

(2) INFORMATION FOR SEQ ID NO:123:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:123:

Ser Ile Asp Ser Thr Thr Phe
1               5

(2) INFORMATION FOR SEQ ID NO:124:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:124:

Gly Pro Ser Arg Val Gly Gly
1               5

(2) INFORMATION FOR SEQ ID NO:125:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:125:

Trp Trp Ser Gly Leu Glu Ala
1               5

(2) INFORMATION FOR SEQ ID NO:126:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:126:

Leu Gly Thr Asp Val Arg Gln
1               5

(2) INFORMATION FOR SEQ ID NO:127:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:127:

Leu Val Gly Val Arg Leu Leu
1           5

(2) INFORMATION FOR SEQ ID NO:128:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:128:

Gly Arg Pro Gly Asp Ile Trp
1           5

(2) INFORMATION FOR SEQ ID NO:129:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:129:

Thr Val Trp Asn Pro Val Gly
1           5

(2) INFORMATION FOR SEQ ID NO:130:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:130:

Gly Leu Leu Leu Val Val Pro
1           5

(2) INFORMATION FOR SEQ ID NO:131:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:131:

Phe Ala Ala Thr Ser Ala Glu
1           5

(2) INFORMATION FOR SEQ ID NO:132:

```
        (i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:132:

Trp Cys Cys Arg Gln Phe Asn
1               5

(2) INFORMATION FOR SEQ ID NO:133:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:133:

Val Gly Phe Gly Lys Ala Leu
1               5

(2) INFORMATION FOR SEQ ID NO:134:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:134:

Asp Ser Ser Leu Arg Leu Pro
1               5

(2) INFORMATION FOR SEQ ID NO:135:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:135:

Lys Leu Trp Cys Ala Met Ser
1               5

(2) INFORMATION FOR SEQ ID NO:136:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:136:

Ser Leu Val Ser Phe Leu Gly
1               5

(2) INFORMATION FOR SEQ ID NO:137:

(i) SEQUENCE CHARACTERISTICS:
            (A) LENGTH: 7 amino acids
            (B) TYPE: amino acid
            (D) TOPOLOGY: both
```

(ii) MOLECULE TYPE: peptide (xi) SEQUENCE DESCRIPTION: SEQ ID NO:137:

Gly Ser Phe Ala Phe Leu Val
1               5

(2) INFORMATION FOR SEQ ID NO:138:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:138:

Ile Ala Ser Val Arg Trp Ala
1               5

(2) INFORMATION FOR SEQ ID NO:139:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:139:

Thr Trp Gly His Leu Arg Ala
1               5

(2) INFORMATION FOR SEQ ID NO:140:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:140:

Gln Tyr Arg Glu Gly Leu Val
1               5

(2) INFORMATION FOR SEQ ID NO:141:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:141:

Gln Ser Ala Asp Arg Ser Val
1               5

(2) INFORMATION FOR SEQ ID NO:142:

(i) SEQUENCE CHARACTERISTICS:
            (A) LENGTH: 7 amino acids
            (B) TYPE: amino acid
            (D) TOPOLOGY: both (ii) MOLECULE TYPE: peptide (xi) SEQUENCE DESCRIPTION: SEQ ID NO:142:

```
Tyr Met Phe Trp Thr Ser Arg
1               5
```

(2) INFORMATION FOR SEQ ID NO:143:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:143:

```
Leu Val Arg Arg Trp Tyr Leu
1               5
```

(2) INFORMATION FOR SEQ ID NO:144:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:144:

```
Thr Ala Arg Gly Ser Ser Arg
1               5
```

(2) INFORMATION FOR SEQ ID NO:145:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:145:

```
Thr Thr Arg Glu Lys Asn Leu
1               5
```

(2) INFORMATION FOR SEQ ID NO:146:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:146:

```
Pro Lys Trp Leu Leu Phe Ser
1               5
```

(2) INFORMATION FOR SEQ ID NO:147:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:147:

```
Leu Arg Thr Asn Val Val His
1               5
```

(2) INFORMATION FOR SEQ ID NO:148:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:148:

```
Ala Val Met Gly Leu Ala Ala
1               5
```

(2) INFORMATION FOR SEQ ID NO:149:

(i) SEQUENCE CHARACTERISTICS:
        (A) LENGTH: 7 amino acids
        (B) TYPE: amino acid
        (D) TOPOLOGY: both (ii) MOLECULE TYPE: peptide (xi) SEQUENCE DESCRIPTION: SEQ ID NO:149:

```
Val Arg Asn Ser Leu Arg Asn
1               5
```

(2) INFORMATION FOR SEQ ID NO:150:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:150:

```
Thr Asp Cys Thr Pro Ser Arg Cys Thr
1               5
```

(2) INFORMATION FOR SEQ ID NO:151:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:151:

```
Ser Trp Cys Gln Phe Glu Lys Cys Leu
1               5
```

(2) INFORMATION FOR SEQ ID NO:152:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:152:

```
Val Pro Cys Arg Phe Lys Gln Cys Trp
1               5
```

(2) INFORMATION FOR SEQ ID NO:153:

(i) SEQUENCE CHARACTERISTICS:

(A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:153:

Cys Thr Ala Met Arg Asn Thr Asp Cys
1               5

(2) INFORMATION FOR SEQ ID NO:154:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:154:

Cys Arg Glu Ser Leu Lys Asn Cys
1               5

(2) INFORMATION FOR SEQ ID NO:155:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:155:

Cys Met Glu Met Gly Val Lys Cys
1               5

(2) INFORMATION FOR SEQ ID NO:156:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:156:

Val Thr Cys Arg Ser Leu Met Cys Gln
1               5

(2) INFORMATION FOR SEQ ID NO:157:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:157:

Cys Asn Asn Val Gly Ser Tyr Cys
1               5

(2) INFORMATION FOR SEQ ID NO:158:

(i) SEQUENCE CHARACTERISTICS:
        (A) LENGTH: 8 amino acids
        (B) TYPE: amino acid
        (D) TOPOLOGY: both

```
        (ii) MOLECULE TYPE: peptide (xi) SEQUENCE DESCRIPTION: SEQ ID NO:158:

Cys Gly Thr Arg Val Asp His Cys
1               5

(2) INFORMATION FOR SEQ ID NO:159:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:159:

Cys Ile Ser Leu Asp Arg Ser Cys
1               5

(2) INFORMATION FOR SEQ ID NO:160:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:160:

Cys Ala Met Val Ser Met Glu Asp
1               5

(2) INFORMATION FOR SEQ ID NO:161:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:161:

Cys Tyr Leu Gly Val Ser Asn Cys
1               5

(2) INFORMATION FOR SEQ ID NO:162:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:162:

Cys Tyr Leu Val Asn Val Asp Cys
1               5

(2) INFORMATION FOR SEQ ID NO:163:

(i) SEQUENCE CHARACTERISTICS:
         (A) LENGTH: 8 amino acids
         (B) TYPE: amino acid
         (D) TOPOLOGY: both (ii) MOLECULE TYPE: peptide (xi) SEQUENCE DESCRIPTION: SEQ ID NO:163:
```

```
Cys Ile Arg Ser Ala Val Ser Cys
1               5
```

(2) INFORMATION FOR SEQ ID NO:164:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:164:

```
Leu Val Cys Leu Pro Pro Ser Cys Glu
1               5
```

(2) INFORMATION FOR SEQ ID NO:165:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:165:

```
Arg His Cys Phe Ser Gln Trp Cys Ser
1               5
```

(2) INFORMATION FOR SEQ ID NO:166:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:166:

```
Phe Tyr Cys Pro Gly Val Gly Cys Arg
1               5
```

(2) INFORMATION FOR SEQ ID NO:167:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:167:

```
Ile Ser Cys Ala Val Asp Ala Cys Leu
1               5
```

(2) INFORMATION FOR SEQ ID NO:168:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:168:

```
Glu Ala Cys Glu Met Ala Gly Cys Leu
1               5
```

(2) INFORMATION FOR SEQ ID NO:169:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:169:

Pro Arg Cys Glu Ser Gln Leu Cys Pro
1               5

(2) INFORMATION FOR SEQ ID NO:170:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:170:

Arg Ser Cys Ile Lys His Gln Cys Pro
1               5

(2) INFORMATION FOR SEQ ID NO:171:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:171:

Gln Trp Cys Ser Arg Arg Trp Cys Thr
1               5

(2) INFORMATION FOR SEQ ID NO:172:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:172:

Met Phe Cys Arg Met Arg Ser Cys Asp
1               5

(2) INFORMATION FOR SEQ ID NO:173:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:173:

Gly Ile Cys Lys Asp Leu Trp Cys Gln
1               5

(2) INFORMATION FOR SEQ ID NO:174:

(i) SEQUENCE CHARACTERISTICS:
        (A) LENGTH: 9 amino acids

```
            (B) TYPE: amino acid
            (D) TOPOLOGY: both (ii) MOLECULE TYPE: peptide (xi) SEQUENCE DESCRIPTION: SEQ ID NO:174:

Asn Ala Cys Glu Ser Ala Ile Cys Gly
1               5

(2) INFORMATION FOR SEQ ID NO:175:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:175:

Ala Pro Cys Gly Leu Leu Ala Cys Ile
1               5

(2) INFORMATION FOR SEQ ID NO:176:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:176:

Asn Arg Cys Arg Gly Val Ser Cys Thr
1               5

(2) INFORMATION FOR SEQ ID NO:177:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:177:

Phe Pro Cys Glu Gly Lys Lys Cys Leu
1               5

(2) INFORMATION FOR SEQ ID NO:178:

(i) SEQUENCE CHARACTERISTICS:
            (A) LENGTH: 9 amino acids
            (B) TYPE: amino acid
            (D) TOPOLOGY: both (ii) MOLECULE TYPE: peptide (xi) SEQUENCE DESCRIPTION: SEQ ID NO:178:

Ala Asp Cys Arg Gln Lys Pro Cys Leu
1               5

(2) INFORMATION FOR SEQ ID NO:179:

(i) SEQUENCE CHARACTERISTICS:
            (A) LENGTH: 9 amino acids
            (B) TYPE: amino acid
            (D) TOPOLOGY: both (ii) MOLECULE TYPE: peptide
```

(xi) SEQUENCE DESCRIPTION: SEQ ID NO:179:

Phe Gly Cys Val Met Ala Ser Cys Arg
1               5

(2) INFORMATION FOR SEQ ID NO:180:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:180:

Ala Gly Cys Ile Asn Gly Leu Cys Gly
1               5

(2) INFORMATION FOR SEQ ID NO:181:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:181:

Arg Ser Cys Ala Glu Pro Trp Cys Tyr
1               5

(2) INFORMATION FOR SEQ ID NO:182:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:182:

Asp Thr Cys Arg Ala Leu Arg Cys Asn
1               5

(2) INFORMATION FOR SEQ ID NO:183:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:183:

Gly Arg Cys Val Asp Gly Gly Cys Thr
1               5

(2) INFORMATION FOR SEQ ID NO:184:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:184:

Tyr Arg Cys Ile Ala Arg Glu Cys Glu 1               5

(2) INFORMATION FOR SEQ ID NO:185:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:185:

Lys Arg Cys Ser Ser Ser Leu Cys Ala
1               5

(2) INFORMATION FOR SEQ ID NO:186:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:186:

Ile Cys Leu Leu Ala His Cys Ala
1               5

(2) INFORMATION FOR SEQ ID NO:187:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:187:

Gln Ala Cys Pro Met Leu Leu Cys Met
1               5

(2) INFORMATION FOR SEQ ID NO:188:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:188:

Leu Asp Cys Leu Ser Glu Leu Cys Ser
1               5

(2) INFORMATION FOR SEQ ID NO:189:

(i) SEQUENCE CHARACTERISTICS:
        (A) LENGTH: 8 amino acids
        (B) TYPE: amino acid
        (D) TOPOLOGY: both (ii) MOLECULE TYPE: peptide (xi) SEQUENCE DESCRIPTION: SEQ ID NO:189:

Ala Gly Cys Arg Val Glu Ser Cys
1               5

(2) INFORMATION FOR SEQ ID NO:190:

(i) SEQUENCE CHARACTERISTICS:
    (A) LENGTH: 9 amino acids
    (B) TYPE: amino acid
    (D) TOPOLOGY: both (ii) MOLECULE TYPE: peptide (xi) SEQUENCE DESCRIPTION: SEQ ID NO:190:

His Thr Cys Leu Val Ala Leu Cys Ala
1               5

(2) INFORMATION FOR SEQ ID NO:191:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:191:

Ile Tyr Cys Pro Gly Gln Glu Cys Glu
1               5

(2) INFORMATION FOR SEQ ID NO:192:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:192:

Arg Leu Cys Ser Leu Tyr Gly Cys Val
1               5

(2) INFORMATION FOR SEQ ID NO:193:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:193:

Arg Lys Cys Glu Val Pro Gly Cys Gln
1               5

(2) INFORMATION FOR SEQ ID NO:194:

(i) SEQUENCE CHARACTERISTICS:
        (A) LENGTH: 9 amino acids
        (B) TYPE: amino acid
        (D) TOPOLOGY: both (ii) MOLECULE TYPE: peptide (xi) SEQUENCE DESCRIPTION: SEQ ID NO:194:

Glu Asp Cys Thr Ser Arg Phe Cys Ser
1               5

(2) INFORMATION FOR SEQ ID NO:195:

(i) SEQUENCE CHARACTERISTICS:
        (A) LENGTH: 9 amino acids
        (B) TYPE: amino acid (D) TOPOLOGY: both (ii) MOLECULE TYPE: peptide (xi) SEQUENCE DESCRIPTION: SEQ ID NO:195:

Leu Glu Cys Val Val Asp Ser Cys Arg
1               5

(2) INFORMATION FOR SEQ ID NO:196:

(i) SEQUENCE CHARACTERISTICS:
          (A) LENGTH: 9 amino acids
          (B) TYPE: amino acid
          (D) TOPOLOGY: both (ii) MOLECULE TYPE: peptide (xi) SEQUENCE DESCRIPTION: SEQ ID NO:196:

Glu Ile Cys Val Asp Gly Leu Cys Val
1               5

(2) INFORMATION FOR SEQ ID NO:197:

(i) SEQUENCE CHARACTERISTICS:
          (A) LENGTH: 9 amino acids
          (B) TYPE: amino acid
          (D) TOPOLOGY: both (ii) MOLECULE TYPE: peptide (xi) SEQUENCE DESCRIPTION: SEQ ID NO:197:

Arg Trp Cys Arg Glu Lys Ser Cys Trp
1               5

(2) INFORMATION FOR SEQ ID NO:198:

(i) SEQUENCE CHARACTERISTICS:
          (A) LENGTH: 9 amino acids
          (B) TYPE: amino acid
          (D) TOPOLOGY: both (ii) MOLECULE TYPE: peptide (xi) SEQUENCE DESCRIPTION: SEQ ID NO:198:

Phe Arg Cys Leu Glu Arg Val Cys Thr
1               5

(2) INFORMATION FOR SEQ ID NO:199:

(i) SEQUENCE CHARACTERISTICS:
          (A) LENGTH: 9 amino acids
          (B) TYPE: amino acid
          (D) TOPOLOGY: both (ii) MOLECULE TYPE: peptide (xi) SEQUENCE DESCRIPTION: SEQ ID NO:199:

Arg Pro Cys Gly Asp Gln Ala Cys Glu
1               5

ANGIOGENIC HOMING MOLECULES AND CONJUGATES DERIVED THEREFROM

This application claims the benefit of priority of U.S. Provisional Application No. 60/060,947, which was converted from U.S. Ser. No. 08/710,067, filed Sep. 10, 1996, the entire contents of which is incorporated herein by reference.

This invention was made with government support under CA 42507, CA 62042, CA74238-01 and Cancer Center Support Grant CA 30199 awarded by the National Institutes of Health. The government has certain rights in this invention.

BACKGROUND OF THE INVENTION

1. Field of the Invention

The present invention relates generally to the fields of cancer biology and drug delivery and, more specifically, to peptides that selectively home to a tumor, particularly a malignant tumor, to compositions comprising an agent such as a therapeutic agent conjugated to such tumor homing molecules, and to methods of using such molecules to target an agent to a tumor.

2. Background Information

Continuous developments over the past quarter century have resulted in substantial improvements in the ability of a physician to diagnose a cancer in a patient. For example, antibody based assays such as that for prostate specific antigen now allow early diagnosis of cancers such as prostate cancer. More recently, methods of genetic screening are becoming available to identify persons that may be particularly susceptible to developing a cancer. Genetic screening methods are based on the identification of one or more mutations in a gene that correlates with the development of a cancer. For example, the identification of genes such as BRCA1 and BRCA2 allowed the further identification of mutations in these genes that, in some cases, can correlate with susceptibility to developing breast cancer.

Unfortunately, methods for treating cancer have not kept pace with those for diagnosing the disease. Thus, while the death rate from various cancers has decreased due to the ability of a physician to detect the disease at an earlier stage, the ability to treat patients presenting with more advanced disease has advanced only minimally.

A major hurdle to advances in treating cancer is the relative lack of agents that can selectively target the cancer, while sparing normal tissue. For example, radiation therapy and surgery, which generally are localized treatments, can cause substantial damage to normal tissue in the treatment field, resulting in scarring and, in severe cases, loss of function of the normal tissue. Chemotherapy, in comparison, which generally is administered systemically, can cause substantial damage to organs such as bone marrow, mucosae, skin and the small intestine, which undergo rapid cell turnover and continuous cell division. As a result, undesirable side effects such as nausea, loss of hair and drop in blood cell count occur as a result of systemically treating a cancer patient with chemotherapeutic agents. Such undesirable side effects often limit the amount of a treatment that can be administered. Thus, cancer remains a leading cause of patient morbidity. and death.

Efforts have been made to increase the target specificity of various drugs. For example, where a unique cell surface marker is expressed by a population of cells making up a tumor, an antibody can be raised against the unique marker and a drug can be linked to the antibody. Upon administration of the drug/antibody complex to the patient, the binding of the antibody to the marker results in the delivery of a relatively high concentration of the drug to the tumor. Similar methods can be used where a particular cancer cell or the supporting cell or matrix expresses a unique cell surface receptor or a ligand for a particular receptor. In these cases, the drug can be linked to the specific ligand or to the receptor, respectively, thus providing a means to deliver a relatively high concentration of the drug to the tumor.

Tumors are characterized, in part, by a relatively high level of active angiogenesis, resulting in the continual formation of new blood vessels to support the growing tumor. Such angiogenic blood vessels are distinguishable from mature vasculature. One of the distinguishing features of angiogenic vasculature is that unique endothelial cell surface markers are expressed. Thus, the blood vessels in a tumor provide a potential target for directing a chemotherapeutic agent to the tumor, thereby reducing the likelihood that the agent will kill sensitive normal tissues. Furthermore, if agents that target the angiogenic blood vessels in a tumor can be identified, there is a likelihood that the agents can be useful against a variety of different types of tumors, since it is the target molecules in the angiogenic vessels that are recognized by such agents and not receptors specific for the tumor cells. However, the use of molecules that can bind specifically to tumor vasculature and target a chemotherapeutic agent to the tumor has not been demonstrated.

While linking a drug to a molecule that homes to a tumor can provide significant advantages for treatment over the use of a drug, alone, use of this method is severely limited by the scarcity of useful cell surface markers expressed in a tumor. Thus, a need exists to identify molecules that can selectively home to a tumor, particularly to the vasculature supporting the tumor. The present invention satisfies this need and provides related advantages as well.

SUMMARY OF THE INVENTION

The present invention relates to molecules that selectively home to tumors, generally to the vasculature supporting the tumor. For example, the invention provides tumor homing peptides that contain, for example, the motif asparagine-glycine-arginine (NGR) or glycine-serine-leucine (GSL), or the $\alpha_v$-containing integrin binding motif, arginine-glycine-aspartic acid (RGD).

The invention also relates to compositions comprising a tumor homing molecule, such as a tumor homing peptide, linked to a moiety to produce a tumor homing molecule/moiety conjugate. Such a moiety can be a drug, for example, a cancer therapeutic agent such as doxorubicin, taxol, cisplatinum, or the like, in which case the tumor homing molecule/moiety conjugate provides a therapeutic reagent. A moiety conjugated to a tumor homing molecule also can be a detectable label, for example, a radionuclide or paramagnetic spin label, such that the molecule/moiety conjugate provides a diagnostic reagent.

The invention also relates to methods of targeting a moiety such as a drug to a tumor by contacting the tumor homing molecule/moiety conjugate with the tumor. Thus, the invention provides methods of diagnosing or treating a cancer in a subject by administering a composition comprising a tumor homing molecule conjugated to a cancer therapeutic agent to the subject. For example, administration of a composition comprising a doxorubicin/CDCRGDCFC (SEQ ID NO: 1) conjugate to a mouse bearing a transplanted breast carcinoma substantially reduced the growth of the breast cancer and the number of metastases and resulted in substantially greater survival as compared to tumor bearing mice treated with doxorubicin, alone, or with doxorubicin conjugated to an unrelated peptide.

The invention further relates to methods of identifying a target molecule in a tumor by detecting selective binding of the target molecule to a tumor homing molecule. For example, a peptide that selectively homes to a tumor can be attached to a solid matrix for use in affinity chromatography. A sample of the tumor can be obtained and passed over the affinity matrix under conditions that allow specific binding of the target molecule, which then can be collected and identified using well known biochemical methods. Thus, the invention also provides a target molecule, which acts as a receptor for a tumor homing molecule. Such a target molecule can be useful, for example, for raising an antibody specific for the target molecule.

BRIEF DESCRIPTION OF THE DRAWINGS

FIGS. 1A, 1C, 1G and 1J are from mice receiving insertless phage (control phage) and FIGS. 1B, 1D, 1E, 1F, 1H, 1I and 1K to 1V are from mice receiving NGR phage. FIGS. 1A, 1B, 1E, 1F and 1G are breast tumor samples; FIGS. 1C, 1D, 1H, 1I and 1J are Kaposi's sarcoma samples; FIG. 1K is brain; FIG. 1L is lymph node; FIG. 1M is kidney; FIG. 1N is pancreas; FIG. 1O is uterus; FIG. 1P is mammary fat pad; FIG. 1Q is lung; FIG. 1R is intestine; FIG. 1S is skin; FIG. 1T is skeletal muscle; FIG. 1U is heart and FIG. 1V is urinary tract epithelium. Magnification: FIGS. 1A to 1D, 40×; FIGS. 1E to 1V, 200×.

DETAILED DESCRIPTION OF THE INVENTION

Figure 1A:
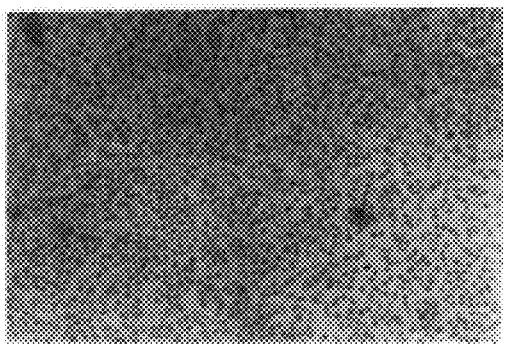
FIGS. 1A to 1V show the immunohistochemical staining of phage expressing the NGR tumor homing peptide, CNGRCVSGCAGRC (SEQ ID NO: 3; "NGR phage"), in tumors and normal tissues following intravenous injection into nude mice bearing a human breast carcinoma or a human Kaposi's sarcoma. Samples were taken 4 min (FIGS. 1E, 1G, 1H and 1J) or 24 hr (FIGS. 1A to 1D, 1F, 1I, and 1K to 1V) after administration of the phage.
Figure 1B:
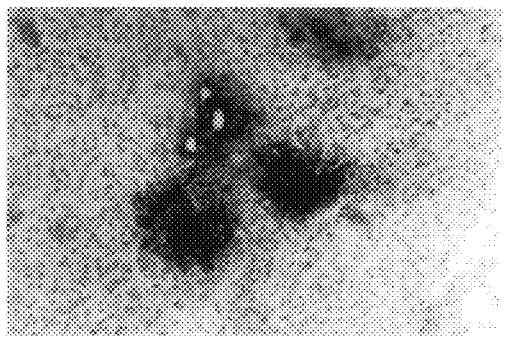
Figure 1C:
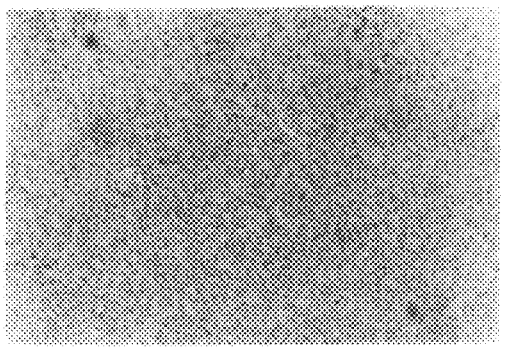

The present invention relates to molecules that selectively home to tumors. For example, the invention provides tumor homing peptides such as the peptides CGRECPRLCQSSC (SEQ ID NO: 2) and CNGRCVSGCAGRC (SEQ ID NO: 3), which were identified based on their ability to home to a breast carcinoma, and the peptide CLSGSLSC (SEQ ID NO: 4, which was identified based on its ability to home to a melanoma. Such tumor homing peptides were identified using in vivo panning (see U.S. Pat. No. 5,622,699, issued Apr. 22, 1997; Pasqualini and Ruoslahti, *Nature* 380:364–366 (1996), each of which is incorporated herein by reference).

The disclosed tumor homing peptides were identified based on their homing to various particular tumors. For example, in vivo panning was performed using a mouse bearing a human breast carcinoma xenograft and peptides that homed to the breast tumor were identified. However, as disclosed herein, such tumor homing peptides generally homed to other types of tumors, including a mouse melanoma and a human Kaposi's sarcoma. Thus, while the tumor homing peptide CNGRCVSGCAGRC (SEQ ID NO: 3) was identified by its ability to home in vivo to a breast tumor, this peptide also homed in vivo to a melanoma and to a Kaposi's sarcoma, but not to nontumor tissues.

Similarly, the tumor homing peptide CLSGSLSC (SEQ ID NO: 4) was identified based on its homing to melanoma. However, further examination of this peptide revealed that it also homed to a breast tumor and to Kaposi's sarcoma. Immunohistological analysis revealed that such tumor homing peptides initially are associated with the vasculature of the various tumors, although at later time the molecules are associated with tumor parenchymal cells. Thus, the general tumor homing ability of a tumor homing molecule of the invention is due, at least in part, to the ability of the tumor homing molecules to target angiogenic vasculature associated with a tumor. These results indicate that specific target molecules are expressed by the cells comprising the vasculature in a tumor as compared to the cell surface molecule expressed by vasculature in nontumor tissues. Using methods as disclosed herein, the artisan readily can determine whether a tumor homing molecule homes generally to the angiogenic vasculature associated with a tumor or homes specifically to a particular type of tumor cell.

As used herein, the term "tumor" means a mass of cells that are characterized, at least in part, by containing angiogenic vasculature. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a "cancer," a tumor also can be nonmalignant, provided that neovascularization is associated with the tumor. The term "normal" or "nontumor" tissue is used to refer to tissue that is not a "tumor." As disclosed herein, a tumor homing molecule can be identified based on its ability to home a tumor, but not to a corresponding nontumor tissue.

As used herein, the term "corresponding," when used in reference to tumors or tissues or both, means that two or more tumors, or two or more tissues, or a tumor and a tissue are of the same histologic type. The skilled artisan will recognize that the histologic type of a tissue is a function of the cells comprising the tissue. Thus, the artisan will recognize, for example, that a nontumor tissue corresponding to a breast tumor is normal breast tissue, whereas a nontumor tissue corresponding to a melanoma is skin, which contains melanocytes. Furthermore, for purposes of the invention, it is recognized that a tumor homing molecule can bind specifically to a target molecule expressed by the vasculature in a tumor, which generally contains blood vessels undergoing neovascularization, in which case a tissue corresponding to the tumor would comprise nontumor tissue containing blood vessels that are not undergoing active angiogenesis.

The term "corresponding" also is used herein in reference to the evolutionarily conserved nature of target molecules, which are expressed in a tumor, for example, in a mouse as compared to a human. Thus, reference to the corresponding target molecules in mouse tumor vasculature as compared, for example, to human vasculature, means target molecules having a similar function, particularly the ability to specifically bind a tumor homing molecule.

Identified tumor homing molecules are useful, for example, for targeting a desired moiety such as a drug, a toxin or a detectable label, which can be linked to the molecule, to a tumor. Thus, the invention provides tumor homing molecule/moiety conjugates, which are useful for targeting the moiety to a tumor. Accordingly, the invention also provides methods of targeting a moiety to a tumor and, therefore, methods of reducing the severity of a tumor and of treating a subject having a cancer (see Example VII). In addition, a tumor homing molecule is useful for identifying the target molecule, to which the homing molecule binds in the tumor.

A tumor homing molecule can be identified by screening a library of molecules by in vivo panning as disclosed herein. As used herein, the term "library" means a collection of molecules. A library can contain a few or a large number of different molecules, varying from about ten molecules to several billion molecules or more. If desired, a molecule can be linked to a tag, which can facilitate recovery or identification of the molecule.

As used herein, the term "molecule" is used broadly to mean an organic chemical such as a drug; a nucleic acid molecule such as an RNA, a cDNA or an oligonucleotide; a peptide, including a variant or modified peptide or peptide-like molecules, referred to herein as peptidomimetics, which mimic the activity of a peptide; or a protein such as an antibody or a growth factor receptor or a fragment thereof such as an Fv, Fd or Fab fragment of an antibody, which contains a binding domain. For convenience, the term "peptide" is used broadly herein to mean peptides, proteins, fragments of proteins and the like. A molecule also can be a non-naturally occurring molecule, which does not occur in nature, but is produced as a result of in vitro methods, or can be a naturally occurring molecule such as a protein or fragment thereof expressed from a cDNA library or a peptidomimetic.

As used herein, the term "peptidomimetic" is used broadly to mean a peptide-like molecule that has the binding activity of the tumor homing peptide. With respect to the tumor homing peptides of the invention, peptidomimetics, which include chemically modified peptides, peptide-like molecules containing non-naturally occurring amino acids, peptoids and the like, have the binding activity of a tumor homing peptide upon which the peptidomimetic is derived (see for example, "Burger's Medicinal Chemistry and Drug Discovery" 5th ed., vols. 1 to 3 (ed. M. E. Wolff; Wiley Interscience 1995), which is incorporated herein by reference). Peptidomimetics provide various advantages over a peptide, including that a peptidomimetic can be stable during passage through the digestive tract and, therefore, useful for oral administration.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a tumor homing molecule, as well as potential geometrical and chemical complementarity to a target molecule bound by a tumor homing peptide. Where no crystal structure of a tumor homing peptide or a target molecule, which binds the tumor homing molecule, is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a tumor homing molecule.

Methods for preparing libraries containing diverse populations of various types of molecules such as peptides, peptoids and peptidomimetics are well known in the art and various libraries are commercially available (see, for example, Ecker and Crooke, Biotechnology 13:351–360 (1995), and Blondelle et al., Trends Anal. Chem. 14:83–92 (1995), and the references cited therein, each of which is incorporated herein by reference; see, also, Goodman and Ro, Peptidomimetics for Drug Design, in "Burger's Medicinal Chemistry and Drug Discovery" Vol. 1 (ed. M. E. Wolff; John Wiley & Sons 1995), pages 803–861, and Gordon et al., J. Med. Chem. 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

A library of molecules also can be produced, for example, by constructing a cDNA expression library from mRNA collected from a cell, tissue, organ or organism of interest. Methods for producing such libraries are well known in the art (see, for example, Sambrook et al., Molecular Cloning: A laboratory manual (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector such as fuse 5 (Example I), wherein, upon expression, the encoded peptide is expressed as a fusion protein on the surface of the phage.

In addition, a library of molecules can comprise a library of nucleic acid molecules, which can be DNA or RNA or an analog thereof. Nucleic acid molecules that bind, for example, to a cell surface receptor are well known (see, for example, O'Connell et al., Proc. Natl. Acad. Sci., USA 93:5883–5887 (1996); Tuerk and Gold, Science 249:505–510 (1990); Gold et al., Ann. Rev. Biochem. 64:763–797 (1995), each of which is incorporated herein by reference). Thus, a library of nucleic acid molecules can be administered to a subject having a tumor and tumor homing molecules can be identified by in vivo panning. If desired, the nucleic acid molecules can be nucleic acid analogs that, for example, are less susceptible to attack by nucleases (see, for example, Jelinek et al., Biochemistry 34:11363–11372 (1995); Latham et al., Nucl. Acids Res. 22:2817–2822 (1994); Tam et al., Nucl. Acids Res. 22:977–986 (1994); Reed et al., Cancer Res. 59:6565–6570 (1990), each of which is incorporated herein by reference).

As disclosed herein, in vivo panning for the purpose of identifying a tumor homing molecule comprises administering a library to a subject, collecting a sample of a tumor and identifying a tumor homing molecule. The presence of a tumor homing molecule can be identified using various methods well known in the art. Generally, the presence of a tumor homing molecule in a tumor is identified based on one or more characteristics common to the molecules present in the library, then the structure of a particular tumor homing molecule is identified. For example, a highly sensitive detection method such as mass spectrometry, either alone or in combination with a method such as gas chromatography, can be used to identify tumor homing molecules in a tumor. Thus, where a library comprises diverse molecules based generally on the structure of an organic molecule such as a drug, a tumor homing molecule can be identified by determining the presence of a parent peak for the particular molecule.

If desired, the tumor can be collected, then processed using a method such as HPLC, which can provide a fraction enriched in molecules having a defined range of molecular weights or polar or nonpolar characteristics or the like, depending, for example, on the general characteristics of the molecules comprising the library. Conditions for HPLC will depend on the chemistry of the particular molecule and are well known to those skilled in the art. Similarly, methods for bulk removal of potentially interfering cellular materials such as DNA, RNA, proteins, lipids or carbohydrates are well known in the art, as are methods for enriching a fraction containing an organic molecule using, for example, methods of selective extraction. Where a library comprises a population of diverse organic chemical molecules, each linked to a specific oligonucleotide tag, such that the specific molecule can be identified by determining the oligonucleotide sequence using polymerase chain reaction (PCR), genomic DNA can be removed from the sample of the collected tumor in order to reduce the potential for background PCR reactions. In addition, a library can comprise a population of diverse molecules such as organic chemical molecules, each linked to a common, shared tag. Based on the presence and properties of the shared tag, molecules of the library that selectively home to a tumor can be substantially isolated from a sample of the tumor. These and other methods can be useful for enriching a sample of a collected tumor for the particular tumor homing molecule, thereby removing potentially contaminating materials from the collected tumor sample and increasing the sensitivity of detecting a molecule.

Evidence provided herein indicates that a sufficient number of tumor homing molecules selectively homes to a tumor during in vivo panning such that the molecules readily can be identified. For example, various independent phage expressing the same peptide were identified in tumors formed from implanted human breast cancer cells (Table 1), from mouse melanoma cells (Table 2) or from human Kaposi's sarcoma cells (Table 3).

Although a substantial fraction of the identified tumor homing molecules have the same structure, the peptide inserts of only a small number of isolated phage were determined. It should be recognized, however, that hundreds of thousands to millions of phage expressing organ homing peptides have been recovered following in vivo pannings for organ homing molecules (see, for example, U.S. Pat. No. 5,622,699; Pasqualini and Ruoslahti, supra, 1996). These results indicate that specific tumor homing molecules will be present in substantial numbers in a tumor following in vivo homing, thereby increasing the ease with which the molecules can be identified.

Ease of identification of a tumor homing molecule, particularly an untagged molecule, depends on various factors, including the presence of potentially contaminating background cellular material. Thus, where the tumor homing molecule is an untagged peptide, a larger number must home to the tumor in order to identify the specific peptides against the background of cellular protein. In contrast, a much smaller number of an untagged organic chemical homing molecule such as a drug is identifiable because such molecules normally are absent from or present in only small numbers in the body. In such a case, a highly sensitive method such as mass spectrometry can be used to identify a tumor homing molecule. The skilled artisan will recognize that the method of identifying a molecule will depend, in part, on the chemistry of the particular molecule.

Where a tumor homing molecule is a nucleic acid or is tagged with a nucleic acid, an assay such as PCR can be particularly useful for identifying the presence of the molecule because, in principle, PCR can detect the presence of a single nucleic acid molecule (see, for example, Erlich, *PCR Technology: Principles and Applications for DNA Amplification* (Stockton Press 1989), which is incorporated herein by reference). Preliminary studies have demonstrated that, following intravenous injection of 10 ng of an approximately 6000 base pair plasmid into a mouse and 2 minutes in the circulation, the plasmid was detectable by PCR in a sample of lung. These results indicate that nucleic acids are sufficiently stable when administered into the circulation such that in vivo panning can be used to identify nucleic acid molecules that selectively home to a tumor.

The molecules of a library can be tagged, which can facilitate recovery or identification of the molecule. As used herein, the term "tag" means a physical, chemical or biological moiety such as a plastic microbead, an oligonucleotide or a bacteriophage, respectively, that is linked to a molecule of the library. Methods for tagging a molecule are well known in the art (Hermanson, *Bioconjugate Techniques* (Academic Press 1996), which is incorporated herein by reference).

A tag, which can be a shared tag or a specific tag, can be useful for identifying the presence or structure of a tumor homing molecule of a library. As used herein, the term "shared tag" means a physical, chemical or biological moiety that is common to each molecule in a library. Biotin, for example, can be a shared tag that is linked to each molecule in a library. A shared tag can be useful to identify the presence of a molecule of the library in a sample and also can be useful to substantially isolate the molecules from a sample. For example, where the shared tag is biotin, the biotin-tagged molecules in a library can be substantially isolated by binding to streptavidin or their presence can be identified by binding with a labeled streptavidin. Where a library is a phage display library, the phage that express the peptides are another example of a shared tag, since each peptide of the library is linked to a phage. In addition, a peptide such as the hemaglutinin antigen can be a shared tag that is linked to each molecule in a library, thereby allowing the use of an antibody specific for the hemaglutinin antigen to substantially isolate molecules of the library from a sample of a selected tumor.

A shared tag also can be a nucleic acid sequence that can be useful to identify the presence of molecules of the library in a sample or to substantially isolate molecules of a library from a sample. For example, each of the molecules of a library can be linked to the same selected nucleotide sequence, which constitutes the shared tag. An affinity column containing a nucleotide sequence that is complementary to the shared tag then can be used to hybridize molecules of the library containing the shared tag, thus substantially isolating the molecules from a tumor sample. A nucleotide sequence complementary to a portion of the shared nucleotide sequence tag also can be used as a PCR primer such that the presence of molecules containing the shared tag can be identified in a sample by PCR.

A tag also can be a specific tag. As used herein, the term "specific tag" means a physical, chemical or biological tag that is linked to a particular molecule in a library and is unique for that particular molecule. A specific tag is particularly useful if it is readily identifiable. A nucleotide sequence that is unique for a particular molecule of a library is an example of a specific tag. For example, the method of synthesizing peptides tagged with a unique nucleotide sequence provides a library of molecules, each containing a specific tag, such that upon determining the nucleotide sequence, the identity of the peptide is known (see Brenner and Lerner, *Proc. Natl. Acad. Sci., USA* 89:5381–5383

(1992), which is incorporated herein by reference). The use of a nucleotide sequence as a specific tag for a peptide or other type of molecule provides a simple means to identify the presence of the molecule in a sample because an extremely sensitive method such as PCR can be used to determine the nucleotide sequence of the specific tag, thereby identifying the sequence of the molecule linked thereto. Similarly, the nucleic acid sequence encoding a peptide expressed on a phage is another example of a specific tag, since sequencing of the specific tag identifies the amino acid sequence of the expressed peptide.

The presence of a shared tag or a specific tag can provide a means to identify or recover a tumor homing molecule of the invention following in vivo panning. In addition, the combination of a shared tag and specific tag can be particularly useful for identifying a tumor homing molecule. For example, a library of peptides can be prepared such that each is linked to a specific nucleotide sequence tag (see, for example, Brenner and Lerner, supra, 1992), wherein each specific nucleotide sequence tag has incorporated therein a shared tag such as biotin. Upon homing to a tumor, the particular tumor homing peptides can be substantially isolated from a sample of the tumor based on the shared tag and the specific peptides can be identified, for example, by PCR of the specific tag (see Erlich, supra, 1989).

A tag also can serve as a support. As used herein, the term "support" means a tag having a defined surface to which a molecule can be attached. In general, a tag useful as a support is a shared tag. For example, a support can be a biological tag such as a virus or virus-like particle such as a bacteriophage ("phage"); a bacterium such as *E. coli*; or a eukaryotic cell such as a yeast, insect or mammalian cell; or can be a physical tag such as a liposome or a microbead, which can be composed of a plastic, agarose, gelatin or other biological or inert material. If desired, a shared tag useful as a support can have linked thereto a specific tag. Thus, the phage display libraries used in the exemplified methods can be considered to consist of the phage, which is a shared tag that also is a support, and the nucleic acid sequence encoding the expressed peptide, the nucleic acid sequence being a specific tag.

In general, a support should have a diameter less than about 10 μm to about 50 μm in its shortest dimension, such that the support can pass relatively unhindered through the capillary beds present in the subject and not occlude circulation. In addition, a support can be nontoxic, so that it does not perturb the normal expression of cell surface molecules or normal physiology of the subject, and biodegradable, particularly where the subject used for in vivo panning is not sacrificed to collect a selected tumor.

Where a molecule is linked to a support, the tagged molecule comprises the molecule attached to the surface of the support, such that the part of the molecule suspected of being able to interact with a target molecule in a cell in the subject is positioned so as to be able to participate in the interaction. For example, where the tumor homing molecule is suspected of being a ligand for a growth factor receptor, the binding portion of the molecule attached to a support is positioned so it can interact with the growth factor receptor on a cell in the tumor. If desired, an appropriate spacer molecule can be positioned between the molecule and the support such that the ability of the potential tumor homing molecule to interact with the target molecule is not hindered. A spacer molecule also can contain a reactive group, which provides a convenient and efficient means of linking a molecule to a support and, if desired, can contain a tag, which can facilitate recovery or identification of the molecule (see Hermanson, supra, 1996).

As exemplified herein, a peptide suspected of being able to home to a selected tumor such as a breast carcinoma or a melanoma was expressed as the N-terminus of a fusion protein, wherein the C-terminus consisted of a phage coat protein. Upon expression of the fusion protein, the C-terminal coat protein linked the fusion protein to the surface of a phage such that the N-terminal peptide was in a position to interact with a target molecule in the tumor. Thus, a molecule having a shared tag was formed by the linking of a peptide to a phage, wherein the phage provided a biological support, the peptide molecule was linked as a fusion protein, the phage-encoded portion of the fusion protein acted as a spacer molecule, and the nucleic acid encoding the peptide provided a specific tag allowing identification of a tumor homing peptide.

As used herein, the term "in vivo panning," when used in reference to the identification of a tumor homing molecule, means a method of screening a library by administering the library to a subject and identifying a molecule that selectively homes to a tumor in the subject (see U.S. Pat. No. 5,622,699). The term "administering to a subject", when used in referring to a library of molecules or a portion of such a library, is used in its broadest sense to mean that the library is delivered to a tumor in the subject, which, generally, is a vertebrate, particularly a mammal such as a human.

A library can be administered to a subject, for example, by injecting the library into the circulation of the subject such that the molecules pass through the tumor; after an appropriate period of time, circulation is terminated by sacrificing the subject or by removing a sample of the tumor (Example I; see, also, U.S. Pat. No. 5,622,699; Pasqualini and Ruoslahti, supra, 1996). Alternatively, a cannula can be inserted into a blood vessel in the subject, such that the library is administered by perfusion for an appropriate period of time, after which the library can be removed from the circulation through the cannula or the subject can be sacrificed to collect the tumor, or the tumor can be sampled, to terminate circulation. Similarly, a library can be shunted through one or a few organs, including the tumor, by cannulation of the appropriate blood vessels in the subject. It is recognized that a library also can be administered to an isolated perfused tumor. Such panning in an isolated perfused tumor can be useful to identify molecules that bind to the tumor and, if desired, can be used as an initial screening of a library.

The use of in vivo panning to identify tumor homing molecules is exemplified herein by screening a phage peptide display library in tumor-bearing mice and identifying specific peptides that selectively homed to a breast tumor or to a melanoma tumor (Example I). However, phage libraries that display protein receptor molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site-directed or codon based mutagenesis (see Huse, U.S. Pat. No. 5,264,563, issued Nov. 23, 1993, which is incorporated herein by reference) and, if desired, peptides can be chemically modified following expression of the phage but prior to administration to the subject. Thus, various types of phage display libraries can be screened by in vivo panning.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (*Meth. Enzymol.* 217:228–257 (1993); see, also, Scott and Smith, *Science* 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference; see, also, Example I). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the in vivo panning method of the invention in order to identify a peptide that homes to a tumor.

In addition to screening a phage display library, in vivo panning can be used to screen various other types of libraries, including, for example, an RNA or DNA library or a chemical library. If desired, the tumor homing molecule can be tagged, which can facilitate recovery of the molecule from the tumor or identification of the molecule in the tumor. For example, where a library of organic molecules, each containing a shared tag, is screened, the tag can be a moiety such as biotin, which can be linked directly to the molecule or can be linked to a support containing the molecules. Biotin provides a shared tag useful for recovering the molecule from a selected tumor sample using an avidin or streptavidin affinity matrix. In addition, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the molecule. Methods for purifying biotin or phOx labeled conjugates are known in the art and the materials for performing these procedures are commercially available (e.g., Invitrogen, La Jolla Calif.; and Promega Corp., Madison Wis.). In the case where a phage library is screened, the phage can be recovered using methods as disclosed in Example I.

In vivo panning provides a method for directly identifying molecules that can selectively home to a tumor. As used herein, the term "home" or "selectively home" means that a particular molecule binds relatively specifically to a target molecule present in the tumor following administration to a subject. In general, selective homing is characterized, in part, by detecting at least a two-fold (2x) greater specific binding of the molecule to the tumor as compared to a control organ or tissue.

It should be recognized that, in some cases, a molecule can localize nonspecifically to an organ or tissue containing a tumor. For example, in vivo panning of a phage display library can result in high background in organs such as liver and spleen, which contain a marked component of the reticuloendothelial system (RES). Thus, where a tumor is present, for example, in the liver, nonspecific binding of molecules due to uptake by the RES can make identifying a tumor homing molecule more difficult.

Selective homing can be distinguished from nonspecific binding, however, by detecting differences in the abilities of different individual phage to home to a tumor. For example, selective homing can be identified by combining a putative tumor homing molecule such as a peptide expressed on a phage with a large excess of non-infective phage or with about a five-fold excess of phage expressing unselected peptides, injecting the mixture into a subject and collecting a sample of the tumor. In the latter case, for example, provided the number of injected phage expressing tumor homing peptide is sufficiently low so as to be nonsaturating for the target molecule, a determination that greater than about 20% of the phage in the tumor express the putative tumor homing molecule is demonstrative evidence that the peptide expressed by the phage is a specific tumor homing molecule. In addition, nonspecific localization can be distinguished from selective homing by performing competition experiments using, for example, phage expressing a putative tumor homing peptide in combination with an excess amount of the "free" peptide (Example IV).

In addition, various methods can be used to prevent nonspecific binding of a molecule to an organ containing a component of the RES. For example, a molecule that homes selectively to a tumor present in an organ containing a component of the RES can be obtained by first blocking the RES using, for example, polystyrene latex particles or dextran sulfate (see Kalin et al., *Nucl. Med. Biol.* 20:171–174 (1993); Illum et al., *J. Pharm. Sci.* 75:16–22 (1986); Takeya et al., *J. Gen. Microbiol.* 100:373–379 (1977), each of which is incorporated herein by reference), then administering the library to the subject. For example, pre-administration of dextran sulfate 500 or polystyrene microspheres prior to administration of a test substance has been used to block nonspecific uptake of the test substance by Kupffer cells, which are the RES component of the liver (Illum et al., supra, 1986). Similarly, nonspecific uptake of agents by the RES has been blocked using carbon particles or silica (Takeya et al., supra, 1977) or a gelatine colloid (Kalin et al., supra, 1993). Thus, various agents useful for blocking nonspecific uptake by the RES are known and routinely used.

Nonspecific binding of phage to RES or to other sites also can be prevented by coinjecting, for example, mice with a specific phage display library together with the same phage made noninfective (Smith et al., supra, 1990, 1993). In addition, a peptide that homes to tumor in an organ containing an RES component can be identified by preparing a phage display library using phage that exhibit low background binding to the particular organ. For example, Merrill et al. (*Proc. Natl. Acad. Sci., USA* 93:3188–3192 (1996), which is incorporated herein by reference) selected lambda-type phage that are not taken up by the RES and, as a result, remain in the circulation for a prolonged period of time. A filamentous phage variant, for example, can be selected using similar methods.

Selective homing can be demonstrated by determining the specificity of a tumor homing molecule for the tumor as compared to a control organ or tissue. Selective homing also can be demonstrated by showing that molecules that home to a tumor, as identified by one round of in vivo panning, are enriched for tumor homing molecules in a subsequent round of in vivo panning. For example, phage expressing peptides that selectively home to a melanoma tumor were isolated by in vivo panning, then were subjected to additional rounds of in vivo panning. Following a second round of screening, phage recovered from the tumor showed a 3-fold enrichment in homing to the tumor as compared to brain. Phage recovered from the tumor after a third round of screening showed an average of 10-fold enrichment in homing to the tumor as compared to brain. Selective homing also can be demonstrated by showing that molecules that home to a selected tumor, as identified by one round of in vivo panning, are enriched for tumor homing molecules in a subsequent round of in vivo panning.

Tumor homing molecules can be identified by in vivo panning using, for example, a mouse containing a transplanted tumor. Such a transplanted tumor can be, for example, a human tumor that is transplanted into immunodeficient mice such as nude mice or a murine tumor that is maintained by passage in tissue culture or in mice. Due to the conserved nature of cellular receptors and of ligands that bind a particular receptor, it is expected that angiogenic vasculature and histologically similar tumor cells in various species can share common cell surface markers useful as target molecules for a tumor homing molecule. Thus, the skilled artisan would recognize that a tumor homing molecule identified using, for example, in vivo panning in a mouse having a murine tumor of a defined histological type such as a melanoma also would bind to the corresponding target molecule in a tumor in a human or other species. Similarly, tumors growing in experimental animals require associated neovascularization, just as that required for a tumor growing in a human or other species. Thus, a tumor homing molecule that binds a target molecule present in the vasculature in a tumor grown in a mouse likely also can bind to the corresponding target molecule in the vasculature of a tumor in a human or other mammalian subject. The general ability of a tumor homing molecule identified, for example, by homing to a human breast tumor, also to home to a human Kaposi's sarcoma or to a mouse melanoma indicates that the target molecules are shared by many tumors. Indeed, the results disclosed herein demonstrate that the target molecules are expressed in the neovasculature, which is host tissue (see Examples IV and VII).

A tumor homing molecule identified using in vivo panning in an experimental animal such as a mouse readily can be examined for the ability to bind to a corresponding tumor in a human patient by demonstrating, for example, that the molecule also can bind specifically to a sample of the tumor obtained from the patient. For example, the CDCRGDCFC (SEQ ID NO: 1) phage and NGR peptides have been shown to bind to blood vessels in microscopic sections of human tumors, whereas little or no binding occurs in the blood vessels of nontumor tissues. Thus, routine methods can be used to confirm that a tumor homing molecule identified using in vivo panning in an experimental animal also can bind the target molecule in a human tumor.

The steps of administering the library to the subject, collecting a selected tumor and identifying the molecules that home to the tumor, comprise a single round of in vivo panning. Although not required, one or more additional rounds of in vivo panning generally are performed. Where an additional round of in vivo panning is performed, the molecules recovered from the tumor in the previous round are administered to a subject, which can be the same subject used in the previous round, where only a part of the tumor was collected.

By performing a second round of in vivo panning, the relative binding selectivity of the molecules recovered from the first round can be determined by administering the identified molecules to a subject, collecting the tumor, and determining whether more phage is recovered from the tumor following the second round of screening as compared to those recovered following the first round. Although not required, a control organ or tissue also can be collected and the molecules recovered from the tumor can be compared with those recovered from the control organ. Ideally, no molecules are recovered from a control organ or tissue following a second or subsequent round of in vivo panning. Generally, however, a proportion of the molecules also will be present in a control organ or tissue. In this case, the ratio of molecules in the selected tumor as compared to the control organ (selected:control) can be determined. For example, phage that homed to melanoma following a first round of in vivo panning demonstrated a 3× enrichment in homing to the selected tumor as compared to the control organ, brain, following two additional rounds of panning (Example V).

Additional rounds of in vivo panning can be used to determine whether a particular molecule homes only to the selected tumor or can recognize a target on the tumor that also is expressed in one or more normal organs or tissues in a subject or is sufficiently similar to the target molecule on the tumor. It is unlikely that a tumor homing molecule also will home to a corresponding normal tissue because the method of in vivo panning selects only those molecules that home to the tumor, which is selected. Where a tumor homing molecule also directs homing to one or more normal organs or tissues in addition to the tumor, the organs or tissues are considered to constitute a family of selected organs or tissues. Using the method of in vivo panning, molecules that home to only the selected tumor can be distinguished from molecules that also home to one or more selected organs or tissues. Such identification is expedited by collecting various organs or tissues during subsequent rounds of in vivo panning.

The term "control organ or tissue" is used to mean an organ or tissue other than the tumor for which the identification of a tumor homing molecule is desired. A control organ or tissue is characterized in that a tumor homing molecule does not selectively home to the control organ. A control organ or tissue can be collected, for example, to identify nonspecific binding of the molecule or to determine the selectivity of homing of the molecule. In addition, nonspecific binding can be identified by administering, for example, a control molecule, which is known not to home to a tumor but is chemically similar to a potential tumor homing molecule. Alternatively, were the administered molecules are linked to a support, administration of the supports, alone, also can be used to identify nonspecific binding. For example, a phage that expresses the gene III protein, alone, but that does not contain a peptide fusion protein, can be studied by in vivo panning to determine the level of nonspecific binding of the phage support.

As disclosed herein, specific homing of a tumor homing molecule readily can be identified by examining the selected tumor tissue as compared to a corresponding nontumor tissue, as well as to control organs or tissues. For example, immunohistological analysis can be performed on a tumor tissue and corresponding nontumor tissue using an antibody specific for a phage used to display tumor homing peptides (see Example IV). Alternatively, an antibody can be used that is specific for a shared tag that expressed with the peptide, for example, a FLAG epitope or the like, such detection systems being commercially available.

In general, a library of molecules, which contains a diverse population of random or selectively randomized molecules of interest, is prepared, then administered to a subject. At a selected time after administration, the subject is sacrificed and the tumor is collected such that the molecules present in the tumor can be identified (see Example I). If desired, one or more control organs or tissues or a part of a control organ or tissue can be sampled. For example, mice bearing a breast tumor or a melanoma tumor were injected with a phage peptide display library, then, after about 1 to 5 minutes, the mice were anesthetized, either frozen in liquid nitrogen or, preferably, are perfused through the heart to terminate circulation of the phage, the tumor and one or more control organs were collected from each, phage present in the tumor and the control organs were recovered and peptides that selectively homed to the respective tumors were identified (see Examples I, II and V).

In the examples provided, the animals were sacrificed to collect the selected tumor and control organ or tissue. It should be recognized, however, that only a part of a tumor need be collected to recover a support containing a molecule that homes to that tumor and, similarly, only part of an organ or tissue need be collected as a control. Thus, a part of a tumor, for example, can be collected by biopsy, such that a molecule such as a peptide expressed by a phage can be administered to the same subject a second time or more, as desired. Where the molecule that is to be administered a second time to the same subject is tagged or linked, for example, to a support, the tag or support should be nontoxic and biodegradable, so as not to interfere with subsequent rounds of screening.

In vitro screening of phage libraries previously has been used to identify peptides that bind to antibodies or to cell surface receptors (Smith and Scott, supra, 1993). For example, in vitro screening of phage peptide display libraries has been used to identify novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994)). However, such in vitro studies provide no insight as to whether a peptide that can specifically bind to a selected receptor in vitro also will bind the receptor in vivo or whether the binding peptide or the receptor are unique to a specific organ in the body. Furthermore, the in vitro methods are performed using defined, well-characterized target molecules in an artificial system. For example, Goodson et al. (supra, 1994) utilized cells expressing a recombinant urokinase receptor. However, such in vitro methods are limited in that they require prior knowledge of the target molecule and yield little if any information regarding in vivo utility.

In vitro panning against cells in culture also has been used to identify molecules that can specifically bind to a receptor expressed by the cells (Barry et al., *Nature Med.* 2:299–305 (1996), which is incorporated herein by reference). However, the cell surface molecules that are expressed by a cell in vivo often change when the cell is grown in culture. Thus, in vitro panning methods using cells in culture also are limited in that there is no guarantee a molecule that is identified due to its binding to a cell in culture will have the same binding ability in vivo. Furthermore, it is not possible using in vitro panning to distinguish molecules that home only to the tumor cells used in the screening, but not to other cell types.

In contrast, in vivo panning requires no prior knowledge or availability of a target molecule and identifies molecules that bind to cell surface target molecules that are expressed in vivo. Also, since the "nontargeted" tissues are present during the screening, the probability of isolating tumor homing molecules that lack specificity of homing is greatly reduced. Furthermore, in obtaining tumor homing molecules by in vivo panning, any molecules that may be particularly susceptible to degradation in the circulation in vivo due, for example, to a metabolic activity, are not recovered. Thus, in vivo panning provides significant advantages over previous methods by identifying molecules that selectively home in vivo and the target molecule present in a tumor.

Although mechanisms by which the disclosed method of in vivo panning works have not been fully defined, one possibility is that a molecule such as a peptide expressed on a phage recognizes and binds to a target molecule present on endothelial cells lining the blood vessels in a tumor. Evidence indicates, for example, that the vascular tissues in various organs differ from one another and that such differences can be involved in regulating cellular trafficking in the body. For example, lymphocytes home to lymph nodes or other lymphoid tissues due, in part, to the expression of specific "address" molecules by the endothelial cells in those tissues (Salmi et al., *Proc. Natl. Acad. Sci., USA* 89:11436–11440 (1992); Springer, *Cell* 76:301–314 (1994)). Similarly, various leukocytes can recognize sites of inflammation due, in part, to the expression of endothelial cell markers induced by inflammatory signals (see Butcher and Picker, *Science* 272:60–66 (1996); Springer, supra, 1994). Thus, endothelial cell markers provide a potential target for directing, for example, a drug, which can be linked to a tumor homing molecule, to a tumor in a subject.

In some cases, the metastasis of cancer cells to specific organs also can be due to recognition by the tumor cell of an organ specific marker, including organ specific endothelial cell markers (Fidler and Hart, *Science* 217:998–1003 (1982)). The pattern of metastasis of many cancers can be explained by assuming that circulating tumor cells are preferentially trapped in the first vascular bed encountered. Thus, the lungs and the liver are the most frequent sites of cancer metastasis. However, some cancers show patterns of metastasis that are not explained by circulatory routing. Metastasis of such cancers may be due to the presence of selectively expressed address molecules such as endothelial cell surface molecules expressed in the organ to which the cancer metastasizes (see Goetz et al., *Int. J. Cancer* 65:192–199 (1996); Zhu et al., *Proc. Natl. Acad. Sci., USA* 88:9568–9572 (1991); Pauli et al., *Cancer Metast. Rev.* 9:175–189 (1990); Nicolson, *Biochim. Biophys. Acta* 948:175–224 (1988)). The identification of molecules that bind to such organ-specific endothelial cell markers can provide a means to prevent tumor cell metastasis to the particular organ.

The vasculature within a tumor generally undergoes active angiogenesis, resulting in the continual formation of new blood vessels to support the growing tumor. Such angiogenic blood vessels are distinguishable from mature vasculature in that angiogenic vasculature expresses unique endothelial cell surface markers, including the $\alpha_v\beta_3$ integrin (Brooks, *Cell* 79:1157–1164 (1994); WO 95/14714, Int. Filing Date Nov. 22, 1994) and receptors for angiogenic growth factors (Mustonen and Alitalo, *J. Cell Biol.* 129:895–898 (1995); Lappi, *Semin. Cancer Biol.* 6:279–288 (1995)). Moreover, tumor vasculature is histologically distinguishable from blood vessel in general in that tumor vasculature is fenestrated (Folkman, *Nature Med.* 1:27–31 (1995); Rak et al., *Anticancer Drugs* 6:3–18 (1995)). Thus, the unique characteristics of tumor vasculature make it a particularly attractive target for determining whether a molecule that homes specifically to a tumor can be identified by in vivo panning. Such a tumor homing molecule can be useful for directing an agent such as a chemotherapeutic drug to a tumor, while reducing the likelihood the agent will have a toxic effect on normal, healthy organs or tissues (Example VII). Moreover, a molecule that homes selectively to tumor vasculature also may have use in targeting other types of neovasculature such as that present in inflammatory, regenerating or wounded tissues.

Using in vivo panning to a breast carcinoma, a melanoma and a Kaposi's sarcoma, phage expressing various peptides that selectively homed to tumors were identified (see Tables 1, 2 and 3, respectively). Due to the large size of the phage 300 nm or 900–1000 nm and the short time the phage were allowed to circulate (3 to 5 min), it is unlikely that a substantial number of phage would have exited the circulatory system, particularly in the brain and kidney. Tissue staining studies indicated that the tumor homing molecules that were identified primarily homed to and bound endothelial cell surface markers, which likely are expressed in an organ-specific manner. These results indicate that in vivo panning can be used to identify and analyze endothelial cell specificities. Such an analysis is not possible using endothelial cells in culture because the cultured cells tend to lose their tissue-specific differences (Pauli and Lee, *Lab. Invest.* 58:379–387 (1988)).

Although the conditions under which the in vivo pannings were performed identified tumor homing peptides that generally bind to endothelial cell markers, the specific presence of phage expressing tumor homing peptides also was observed in tumor parenchyma, particularly at later times after administration of the peptides (Example IV). These results demonstrate that phage expressing peptides can pass through the blood vessels in the tumor, possibly due to the fenestrated nature of the blood vessels, and indicate that the in vivo panning method can be useful for identifying target molecules expressed by tumor cells, as well as target molecules expressed by endothelial cells.

Phage peptide display libraries were constructed essentially as described Smith and Scott (supra, 1993; see, also, Koivunen et al., *Biotechnology* 13:265–270 (1995); Koivunen et al., *Meth. Enzymol.* 245:346–369 (1994b), each of which is incorporated herein by reference). Oligonucleotides encoding peptides having substantially random amino acid sequences were synthesized based on an "NNK" codon, wherein "N" is A, T, C or G and "K" is G or T. "NNK" encodes 32 triplets, which encode the twenty amino acids and an amber STOP codon (Scott and Smith, supra, 1990). In some libraries, at least one codon encoding cysteine also was included in each oligonucleotide so that cyclic peptides could be formed through disulfide linkages (Example I). The oligonucleotides were inserted in frame with the sequence encoding the gene III protein (gIII) in the vector fuse 5 such that a peptide-gIII fusion protein can be expressed. Following expression, the fusion protein is expressed on the surface of the phage containing the vector (Koivunen et al., supra, 1994b; Smith and Scott, supra, 1993).

Following in vivo panning, the phage isolated based on their ability to selectively home to human breast carcinoma, mouse melanoma or human Kaposi's sarcoma tumors displayed only a few different peptide sequences (see Tables 1, 2 and 3, respectively). One of the screenings revealed peptide sequences that contained the arginine-glycine-aspartic acid (RGD) integrin recognition sequence (Ruoslahti, *Ann. Rev. Cell Devel. Biol.* 12:697 (1996)) in the context of a peptide previously demonstrated to bind selectively to $\alpha_v$-containing integrins (Koivunen et al., supra, 1995; WO 95/14714). The sequences of most of the remaining tumor homing peptides did not reveal any significant similarities with known ligands for endothelial cell receptors. However, one of the tumor homing peptides contained the asparagine-glycine-arginine (NGR) motif, which is a weak integrin binding motif similar to the motifs present in integrin-binding peptides (Ruoslahti et al., U.S. Pat. No. 5,536,814, issued Jul. 16, 1996, which is incorporated herein by reference; see, also, Koivunen et al., supra, 1994a). Other screenings have revealed numerous NGR-containing peptides (see Table 1). Despite the weak integrin binding ability of NGR peptides, an integrin receptor may not be the target molecule recognized by the NGR tumor homing peptides exemplified herein (Example VII). As used herein, the term "integrin" means a heterodimeric cell surface adhesion receptor.

The peptides expressed by the phage that homed to the breast tumor included the peptides CGRECPRLCQSSC (SEQ ID NO: 2) and CNGRCVSGCAGRC (SEQ ID NO: 3; see Table 1; Example II). Similarly, tumor homing peptides, including the peptides CDCRGDCFC (SEQ ID NO: 1) and CGSLVRC (SEQ ID NO: 5), were identified from two other phage libraries administered to breast tumor bearing mice (Table 1). Some of these motifs, as well as novel one, also were isolated in the screen with mouse melanoma and human Kaposi's sarcoma (see Tables 2 and 3). These results demonstrated that tumor homing molecules can be identified using in vivo panning.

Three main tumor homing motifs emerged. As discussed above, one motif contained the sequence RGD (Ruoslahti, supra, 1996) embedded in the peptide structure, CDCRGDCFC (SEQ ID NO: 1), which is known to bind selectively to $\alpha_v$ integrins (Koivunen et al., supra, 1995; WO 95/14714). Since the $\alpha_v\beta_3$ and $\alpha_v\beta_5$ integrins are markers of angiogenic vessels (Brooks et al., supra, 1994; Friedlander et al., *Science* 270:1500 (1995)), a phage expressing the peptide CDCRGDCFC (SEQ ID NO: 1) was examined for tumor targeting and, as disclosed herein, homed to tumors in a highly selective manner (see Example III). Furthermore, homing by the CDCRGDCFC (SEQ ID NO: 1) phage was inhibited by coadministration of the free CDCRGDCFC (SEQ ID NO: 1) peptide.

Another breast tumor homing peptide had the sequence CNGRCVSGCAGRC (SEQ ID NO: 3), which contains the NGR motif previously shown to have weak integrin binding activity (Koivunen et al., *J. Biol. Chem.* 268:20205–20210 (1993); Koivunen et al., supra, 1994a; WO 95/14714). Since an NGR containing peptide was identified, two additional peptides, the linear peptide, NGRAHA (SEQ ID NO: 6), and the cyclic peptide, CVLNGRMEC (SEQ ID NO: 7), each of which contains the NGR motif, were examined for tumor homing. Like the phage expressing CNGRCVSGCAGRC (SEQ ID NO: 3), phage expressing NGRAHA (SEQ ID NO: 6) or CVLNGRMEC (SEQ ID NO: 7) homed to the tumors. Furthermore, tumor homing was not dependent on the tumor type or on species, as the phage accumulated selectively in human breast carcinoma, as well as in the tumors of mice bearing a mouse melanoma and mice bearing a human Kaposi's sarcoma xenograft.

The various peptides, including RGD- and NGR-containing peptides, generally were bound to the tumor blood vessels. The minimal cyclic NGR peptide, CNGRC (SEQ ID NO: 8), was synthesized based on the CNGRCVSGCAGRC (SEQ ID NO: 3) sequence. When the CNGRC (SEQ ID NO: 8) peptide was co-injected with phage expressing either CNGRCVSGCAGRC (SEQ ID NO: 3), NGRAHA (SEQ ID NO: 6) or CVLNGRMEC (SEQ ID NO: 7), accumulation of the phage in the breast carcinoma xenografts was inhibited. However, the CNGRC (SEQ ID NO: 8) peptide did not inhibit the homing of phage expressing the CDCRGDCFC (SEQ ID NO: 1) peptide, even when administered in amounts up to ten times higher than those that inhibited the homing of the NGR phage. In comparison, the CDCRGDCFC (SEQ ID NO: 1) peptide partially inhibited the homing of the NGR phage, although the amount needed was 5 to 10 fold higher than that of the CNGRC peptide (SEQ ID NO: 8). These results indicate that NGR peptides and RGD peptides bind to different receptor sites in tumor vasculature.

A third motif, GSL (glycine-serine-leucine), also was identified following in vivo panning in mice bearing breast carcinoma, malignant melanoma. or Kaposi's sarcoma. Homing of phage expressing the GSL peptide, CGSLVRC (SEQ ID NO: 5), was inhibited by coadministration of the free CGSLVRC (SEQ ID NO: 5) peptide. Like the RGD and NGR peptides, phage expressing GSL peptides also bound to blood vessels of tumors. In view of the identification of the conserved RGD, NGR and GSL motifs present in tumor homing peptides, as disclosed herein, it will be recognized that peptides containing such motifs can be useful as tumor homing peptides and, in particular, for forming conjugates that can target a moiety such as a cancer chemotherapeutic agent or a diagnostic agent to a tumor.

Various peptide libraries containing up to 13 amino acids were constructed and the NGR peptide, CNGRCVSG-CAGRC (SEQ ID NO: 3), was obtained as a result of in vivo panning against a breast tumor. This NGR peptide, which was obtained by screening a random peptide library, was a tumor homing peptide (see Example VII). In addition, when a peptide library was constructed based on the formula CXXXNGRXX (SEQ ID NO: 13) or CXXCNGRCX (SEQ ID NO: 14), each of which is biased toward NGR sequences, and used for in vivo panning against a breast tumor, numerous NGR peptides were obtained (see Table 1).

These results indicate that a tumor homing peptide of the invention can comprise the amino acid sequence RGD or NGR or GSL. Such tumor peptides can be as small as five amino acids, such as CNGRC (SEQ ID NO: 8). Such tumor homing peptides also can be not only at least 13 amino acids in length, which is the largest peptide exemplified herein, but can be up to 20 amino acids, or 30 amino acids, or 50 to 100 amino acids in length, as desired. A tumor homing peptide of the invention conveniently is produced by chemical synthesis.

Immunohistochemical analysis was performed by comparing tissue staining for phage allowed to circulate for about four minutes, followed by perfusion through the heart of the mice, or with tissues analyzed 24 hours after phage injection (see FIG. 1). At 24 hours following administration, essentially no phage remain in the circulation and, therefore, perfusion is not required (Pasqualini et al., supra, 1997). Strong phage staining was observed in tumor vasculature, but not in normal endothelium, in samples examined four minutes after administration of the CNGRCVSGCAGRC (SEQ ID NO: 3) phage (Example IV; compare FIGS. 1E, 1G, 1H and 1J). In comparison, staining of the tumor was strong at 24 hours and appeared to have spread outside the blood vessels into the tumor parenchyma (compare FIGS. 1A to 1D and 1F (tumor) with FIGS. 1I and 1K to 1V (nontumor)). The NGRAHA (SEQ ID NO: 6) and CVLN-GRMEC (SEQ ID NO: 7) phage showed similar staining patterns (Example IV). In contrast, the control organs and tissues showed little or no immunostaining, confirming the specificity of the NGR motifs for tumor vessels. Spleen and liver, however, captured phage, as expected, since uptake by the reticuloendothelial system is a general property of phage particles, independent of the presence of peptide expression by the phage (Pasqualini et al., supra, 1997).

Immunostaining also was observed following administration of phage expressing the GSL motif containing peptide, CLSGSLSC (SEQ ID NO: 4), and, like that of the NGR peptides, was localized to the blood vessels, in this case, within a melanoma tumor (see below; see, also, Examples IV and V). Similarly, immunostaining following administration of phage expressing the RGD motif containing peptide, CDCRGDCFC (SEQ ID NO: 1), to breast tumor bearing mice was localized to the blood vessels in the tumor, but was not observed in brain, kidney or various other nontumor tissues (see Examples III and IV; see, also, Pasqualini et al., supra, 1997). These results demonstrate that the various tumor homing peptides generally home to tumor vasculature.

The general applicability of the in vivo panning method for identifying molecules that home to a tumor was examined by injecting mice bearing a syngeneic melanoma with phage expressing a diverse population of peptides (Example V). The B16 mouse melanoma model was selected for these studies because the tumors that form are highly vascularized and because the biology of this tumor line. has been thoroughly characterized (see Miner et al., *Cancer Res.* 42:4631–4638 (1982)). Furthermore, because the B16 melanoma cells are of mouse origin, species differences between the host and the tumor cell donor will not affect, for example, the distribution of phage into the tumor as compared to into normal organs. As disclosed herein, in vivo panning against B16 melanoma cells revealed tumor homing peptides, including, for example, the GSL moiety containing peptide CLSGSLSC (SEQ ID NO: 4; see, also, Table 2) and immunohistochemical staining of the tumor and other organs using an anti-phage antibody demonstrated that the CLSGSLSC (SEQ ID NO: 4) expressing phage resulted in immunostaining in the melanoma, but essentially no staining in skin, kidney or other control organs (Example V). The staining pattern generally followed the blood vessels within the melanoma, but was not strictly confined to the blood vessels.

Although in vivo panning was performed in mice, at least the peptides comprising an NGR, RGD or GSL motif also likely can target human vasculature. The NGR phage binds to blood vessels in the transplanted human breast tumor, but not to blood vessels in normal tissues, indicating that this motif can be particularly useful for tumor targeting in patients. The CDCRGDCFC (SEQ ID NO: 1) peptide binds to human $\alpha_v$-integrins (Koivunen et al., supra, 1995), which are selectively expressed in tumor blood vessels of human patients (Max et al., *Int. J. Cancer* 71:320 (1997); Max et al., *Int. J. Cancer* 72:706 (1997)). Use of a moiety/CDCRGDCFC (SEQ ID NO: 1) conjugate to target the moiety to a tumor also provides the additional advantage that the moiety will be targeted to tumor cells, themselves, because breast carcinoma cells, for example, can express the $\alpha_v\beta_3$ integrin (Pasqualini et al., supra, 1997). In fact, many human tumors express this integrin, which may be involved in the progression of certain tumors such as malignant melanomas (Albelda et al., *Cancer Res.* 50:6757–6764 (1990); Danen et al., *Int. J. Cancer* 61:491–496 (1995); Felding-Habermann et al., *J. Clin. Invest.* 89:2018–2022 (1992); Sanders et al., *Cold Spring Harb. Symp. Quant. Biol.* 58:233–240 (1992); Mitjans et al., *J. Cell. Sci.* 108:3067–3078 (1995)). Unlike the CDCRGDCFC (SEQ ID NO: 1) peptide, the NGR peptides do not appear to bind to MDA-MD-435 breast carcinoma cells. However, NGR peptides were able to deliver a therapeutically effective amount of doxorubicin to breast tumors (Example VII), indicating that, even where a tumor homing molecule homes only to tumor vasculature, i.e., not directly to the tumor cells, such vasculature targeting in sufficient to confer the effect of the moiety linked to the molecule.

Since the $\alpha_v\beta_3$ integrin is expressed by endothelial cells in angiogenic vasculature, experiments were performed to determine whether tumor vasculature that is undergoing angiogenesis can be targeted in vivo using methods as disclosed herein. Phage expressing the peptide, CDCRGDCFC (SEQ ID NO: 1; see, Koivunen et al., supra, 1995), which is known to bind to the $\alpha_v\beta_3$ integrin, were injected into mice bearing tumors formed from human breast carcinoma cells, mouse melanoma cells or human Kaposi's sarcoma cells (see Example IV). The CDCRGDCFC (SEQ ID NO: 1) phage selectively homed to each of the tumors, whereas such homing did not occur with control phage. For example, in mice bearing tumors formed by implantation of human breast carcinoma cells, a twenty- to eighty-fold greater number of the CDCRGDCFC (SEQ ID NO: 1) phage, as compared to unselected control phage, accumulated in the tumor.

Tissue staining for the phage showed accumulation of the CDCRGDCFC (SEQ ID NO: 1) phage in the blood vessels within the tumor, whereas no staining was observed in brain, kidney or other control organs. Specificity of tumor homing by the CDCRGDCFC (SEQ ID NO: 1) phage was demonstrated by competition experiments, in which coinjection of the free CDCRGDCFC (SEQ ID NO: 1) peptide greatly reduced tumor homing of the RGD phage, whereas coinjection of a non-RGD-containing control peptide had no effect on homing of the RGD phage (see Example III). These results demonstrate that the $\alpha_v\beta_3$ target molecule is expressed on the luminal surface of endothelial cells in a tumor and that a peptide that binds to an $\alpha_v$-containing integrin can bind selectively to this integrin and, therefore, to vasculature undergoing angiogenesis.

The results of these studies indicate that tumor homing molecules can be identified by in vivo panning and that, in some cases, a tumor homing molecule can home to vascular tissue in the tumor as well as to tumor parenchyma, probably due to the fenestrated nature of the blood vessels permitting ready exit of the phage from the circulatory system. Due to the ability of such tumor homing molecules to home to tumors, the molecules are useful for targeting a linked moiety to tumors. Thus, the invention provides conjugates comprising a tumor homing molecule linked to a moiety, such conjugates being useful for targeting the moiety to tumor cells.

The ability of a molecule that homes to a particular tumor to selectively home to another tumor of the same or a similar histologic type can be determined using, for example, human tumors grown in nude mice or mouse tumors grown in syngeneic mice for these experiments. For example, various human breast cancer cell lines, including MDA-MB-435 breast carcinoma (Price et al., *Cancer Res.* 50:717–721 (1990)), SKBR-1-II and SK-BR-3 (Fogh et al., *J. Natl. Cancer Inst.* 59:221–226 (1975)), and mouse mammary tumor lines, including EMT6 (Rosen et al., *Int. J. Cancer* 57:706–714 (1994)) and C3-L5 (Lala and Parhar, *Int. J. Cancer* 54:677–684 (1993)), are readily available and commonly used as models for human breast cancer. Using such breast tumor models, for example, information relating to the specificity of an identified breast tumor homing molecule for diverse breast tumors can be obtained and molecules that home to a broad range of different breast tumors or provide the most favorable specificity profiles can be identified. In addition, such analyses can yield new information, for example, about tumor stroma, since stromal cell gene expression, like that of endothelial cells, can be modified by the tumor in ways that cannot e reproduced in vitro.

Selective homing of a molecule such as a peptide or protein to a tumor can be due to specific recognition by the peptide of a particular cell target molecule such as a cell surface receptor present on a cell in the tumor. Selectivity of homing is dependent on the particular target molecule being expressed on only one or a few different cell types, such that the molecule homes primarily to the tumor. As discussed above, the identified tumor homing peptides, at least in part, can recognize endothelial cell surface markers in the blood vessels present in the tumors. However, most cell types, particularly cell types that are unique to an organ or tissue, can express unique target molecules. Thus, in vivo panning can be used to identify molecules that selectively home to a particular type of tumor cell such as a breast cancer cell and specific homing can be demonstrated by performing the appropriate competition experiments.

A tumor homing molecule of the invention can be used to target a moiety to a tumor by linking the moiety to the molecule to produce a tumor homing molecule/moiety conjugate and administering the conjugate to a subject having a tumor. As used herein, the term "moiety" is used broadly to mean a physical, chemical, or biological material that is linked to a tumor homing molecule for the purpose of being targeted in vivo to a tumor or to angiogenic vasculature expressing a target molecule recognized by the tumor homing molecule. In particular, a moiety is a biologically useful moiety such as therapeutic moiety, a diagnostic moiety or a drug delivery vehicle. Thus, a moiety can be a therapeutic agent, for example, a cancer chemotherapeutic agent such as doxorubicin, which, when linked to a tumor homing molecule, provides a conjugate useful for treating a cancer in a subject. In addition, a moiety can be a drug delivery vehicle such as a chambered microdevice, a cell, a liposome or a virus, which can contain an agent such as a drug or a nucleic acid.

A moiety also can be a molecule such as a polypeptide or nucleic acid, to which a tumor homing molecule is grafted for the purpose of directing the polypeptide or nucleic acid to a selected tumor (Smith et al., *J. Biol. Chem.* 269:32788–32,795(1994); Goldman et al., *Cancer Res.* 15:1447–1451 (1997), each of which is incorporated herein by reference). For example, a peptide tumor homing molecule can be expressed as a fusion protein with a desired polypeptide such that the peptide targets the grafted polypeptide to a selected tumor. Such a desired polypeptide, which is grafted to the tumor homing peptide, can be a polypeptide involved in initiating a cell death pathway, for example, caspase 8, thus providing a means to direct caspase 8 to a tumor, where it can induce apoptosis of the tumor cells or of the vasculature supplying the tumor. A tumor homing peptide also can be grafted to a polypeptide expressed by a virus, for example, the adenovirus penton base coat protein, thus providing a means to target a virus to a tumor (Wickham et al., *Gene Ther.* 2:750–756 (1995); Weitzman et al., In: "Gene Therapy and Vector Systems" 2:17–25 (1997), each of which is incorporated herein by reference; see, also, Example III). Such a grafted virus can contain an exogenous gene useful in a method of gene therapy. Accordingly, the invention provides compositions of matter comprising a tumor homing molecule/moiety conjugate.

A moiety can be a detectable label such a radiolabel or can be a cytotoxic agent, including a toxin such as ricin or a drug such as a chemotherapeutic agent or can be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to a molecule of the invention are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988), each of which is incorporated herein by reference; see, also, Hermanson, supra, 1996).

As disclosed herein, a moiety can be, for example, a cancer chemotherapeutic agent linked to a tumor homing molecule to produce a tumor homing molecule/moiety conjugate. Cytotoxic chemotherapy is the basis of the systemic treatment of disseminated malignant tumors. However, a major limitation of the currently used chemotherapeutic agents is that these drugs have the narrowest therapeutic index in all of medicine. As such, the dose of cancer chemotherapeutic agents generally is limited by undesirable toxicity to the patient being treated. Thus, the ability of tumor homing peptides of the invention to target drugs into tumors was examined. As disclosed herein, the linking of a cancer chemotherapeutic agent, doxorubicin, to a tumor homing molecule reduced the systemic toxicity of the doxorubicin and enhanced anti-tumor activity of the agent (see Example VII).

A conjugate of the invention is exemplified herein by doxorubicin linked to various tumor homing peptides (see Examples VI and VII). In view of the exemplified method of linking doxorubicin to various tumor homing peptides and the disclosed efficacy of such conjugates of the invention, the skilled artisan will recognize that various other chemotherapeutic agents also can be linked to a tumor homing molecule to make a conjugate of the invention. Cancer chemotherapeutic agents have been linked to antibodies, for example, for the purpose of targeting the agents to cells such as tumor cells that express the antigen recognized by the antibodies. In addition, in such antibody/drug conjugates, the agent can maintain its therapeutic function and the antibody can maintain its antigen binding specificity. For example, the anthracyclin, doxorubicin, has been linked to antibodies and the antibody/doxorubicin conjugates have been therapeutically effective in treating tumors (Sivam et al., *Cancer Res.* 55:2352–2356 (1995); Lau et al., *Bioorg. Med. Chem.* 3:1299–1304 (1995); Shih et al., *Cancer Immunol. Immunother.* 38:92–98 (1994)). Similarly, other anthracyclins, including idarubicin and daunorubicin, have been chemically conjugated to antibodies, which have delivered effective doses of the agents to tumors (Rowland et al., *Cancer Immunol. Immunother.* 37:195–202 (1993); Aboud-Pirak et al., *Biochem. Pharmacol.* 38:641–648 (1989)).

In addition to the anthracyclins, alkylating agents such as melphalan and chlorambucil have been linked to antibodies to produce therapeutically effective conjugates (Rowland et al., supra, 1994; Smyth et al., *Immunol. Cell Biol.* 65:315–321 (1987)), as have vinca alkaloids such as vindesine and vinblastine (Aboud-Pirak et al., supra, 1989; Starling et al., *Bioconj. Chem.* 3:315–322 (1992)). Similarly, conjugates of antibodies and antimetabolites such as 5-fluorouracil, 5-fluorouridine and derivatives thereof have been effective in treating tumors (Krauer et al., *Cancer Res.* 52:132–137 (1992); Henn et al., *J. Med. Chem.* 36:1570–1579 (1993)). Other chemotherapeutic agents, including cis-platinum (Schechter et al., *Int. J. Cancer* 48:167–172 (1991)), methotrexate (Shawler et al., *J. Biol. Resp. Mod.* 7:608–618 (1988); Fitzpatrick and Garnett, *Anticancer Drug Des.* 10:11–24 (1995)) and mitomycin-C (Dillman et al., *Mol. Biother.* 1:250–255 (1989)) also are therapeutically effective when administered as conjugates with various different antibodies.

The results obtained using antibody/drug conjugates demonstrate that a chemotherapeutic agent can be linked to an antibody to produce a conjugate that maintains the antigen binding specificity of the antibody and the therapeutic function of the agent. As disclosed herein, a conjugate comprising doxorubicin and a tumor homing peptide maintains the tumor homing specificity of the tumor homing peptide as well as the therapeutic efficacy of the chemotherapeutic agent (see Example VII). Such results are remarkable, since, in the doxorubicin/CNGRC (SEQ ID NO: 8) conjugate, for example, the doxorubicin component has only a slightly lower molecular weight than the peptide and comprises about 46% of the molecular weight of the conjugate.

Since the moiety component of a tumor homing molecule/moiety conjugate can comprise a substantial portion of the conjugate without adversely affecting the ability of the tumor homing molecule to home to a tumor, additional components can be included as part of the conjugate, if desired. For example, in some cases, it can be desirable to utilize an oligopeptide spacer between a tumor homing peptide and the moiety (Fitzpatrick and Garnett, *Anticancer Drug Des.* 10:1–9 (1995)). In this way, panels of moiety/spacer complexes can be constructed, in which a common spacer is linked to various different moieties. Such panels of moiety/spacer conjugates can facilitate linkage of the moiety to a tumor homing molecule such as a tumor homing peptide of choice.

Doxorubicin is one of the most commonly used cancer chemotherapeutic agents and, particularly, is used for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449–454 (eds. Steiner et al.; Birkhauser Verlag, 1992)), which can contribute to its effectiveness in treating cancer. Thus, treatment of human breast cancer xenografts in mice using doxorubicin was selected as a model for exemplifying the present invention.

CDCRGDCFC (SEQ ID NO: 1) and CNGRC (SEQ ID NO: 8) were coupled to doxorubicin (Example VI) and the peptide/doxorubicin conjugates were used to treat mice bearing tumors derived from human MDA-MB-435 breast carcinoma cells (Example VII). Mice were treated with 5 $\mu$g/week of doxorubicin equivalent (i.e., either free doxorubicin or the doxorubicin component of the peptide/doxorubicin conjugate), as compared to the more commonly used 50–200 $\mu$g/mouse used in tumor bearing mice (Berger et al., In "The Nude Mouse in Oncology Research" (CRC Press 1991)). The lower dose was selected because it was expected that the conjugate would be more effective than the free drug.

MDA-MB-435 tumor-bearing mice treated with the doxorubicin/CDCRGDCFC (SEQ ID NO: 1) conjugate had significantly smaller tumors, less spread to regional lymph nodes, and fewer pulmonary metastasis than mice treated with free doxorubicin (see Example VII). All of the mice treated with the doxorubicin/CDCRGDCFC (SEQ ID NO: 1) conjugate survived beyond the time when all of the mice treated with free doxorubicin had died from widespread disease. In a dose-escalation experiment, the tumor bearing mice were treated with the doxorubicin/CDCRGDCFC (SEQ ID NO: 1) conjugate at 30 $\mu$g/mouse every three weeks for three cycles, then were observed, without further treatment, for an extended period of time. The conjugate treated mice all remained alive more than 6 months after the control, doxorubicin treated mice had died (Example VII). These results indicate that primary tumor growth and metastasis significantly were inhibited in mice treated with the conjugate and that cures may have occurred.

Many of the mice that received doxorubicin/CDCRGDCFC (SEQ ID NO: 1) conjugate presented marked skin ulceration and tumor necrosis; no such signs were observed in mice treated with free doxorubicin or with doxorubicin conjugated to an unrelated peptide (Example VII). Histopathological analysis disclosed a pronounced destruction of the vasculature in the tumors treated with conjugate as compared to mice treated with free doxorubicin. Furthermore, when tumors were removed from the mice and the tumor cells plated in culture, viability of cells from the tumors of mice receiving the doxorubicin/CDCRGDCFC (SEQ ID NO: 1) conjugate was about 3 fold less than cells from tumors of mice treated with the free doxorubicin (see Example VII). These results demonstrate that administration to a tumor bearing mouse of a conjugate comprising a chemotherapeutic agent linked to a tumor homing molecule is more efficacious than administration of the agent, alone, in treating a tumor.

Toxicity was determined by administration of 200 µg/doxorubicin equivalent in mice with very large, size matched breast tumors. All of the mice treated with the doxorubicin/CDCRGDCFC (SEQ ID NO: 1) conjugate survived more than a week, while all of the mice treated with free doxorubicin died within 48 hours of the administration of the drug (Example VII). These results indicate that accumulation of the tumor homing peptide/doxorubicin conjugate in the large tumors can reduce systemic toxicity of the agent.

Similar toxicity and treatment efficacy results were obtained when breast tumor bearing mice were treated using a doxorubicin/CNGRC (SEQ ID NO: 8) conjugate. Tumors in the mice treated with the CNGRC (SEQ ID NO: 8) conjugate were significantly smaller than in the control groups; the conjugate suppressed tumor growth almost completely. A strong effect on survival also occurred. Free doxorubicin or doxorubicin conjugated to an unrelated peptide, at the dose used, had little if any effect on tumor growth relative to vehicle alone.

Cytotoxic activity of free doxorubicin and the doxorubicin/peptide conjugates was compared in vitro using MDA-MB-435 cells. When cells were exposed to free doxorubicin, doxorubicin/CDCRGDCFC (SEQ ID NO: 1) or doxorubicin conjugated to an unrelated peptide for 30 minutes, cell death occurred only in the cultures treated with the doxorubicin/CDCRGDCFC (SEQ ID NO: 1) conjugate. In comparison, cells were killed by all of the treatments after 24 hours of exposure. These results indicate that enhanced cellular uptake of the doxorubicin/CDCRGDCFC (SEQ ID NO: 1) conjugate occurs.

As disclosed herein, tumor homing molecules of the invention can bind to the endothelial lining of small blood vessels of tumors. The vasculature within tumors is distinct, presumably due to the continual neovascularization, resulting in the formation of new blood vessels required for tumor growth. The distinct properties of the angiogenic neovasculature within tumors are reflected in the presence of specific markers in endothelial cells and pericytes (Folkman, *Nature Biotechnol.* 15:510 (1997); Risau, *FASEB J.* 9:926–933 (1995); Brooks et al., supra, 1994); these markers likely are being targeted by the tumor homing molecules of the invention.

The ability of a tumor homing molecule to target the blood vessels in a tumor provides substantial advantages over methods of systemic treatment or methods that directly target the tumor cells. For example, tumor cells depend on a vascular supply for survival and the endothelial lining of blood vessels is readily accessible to a circulating probe. Conversely, in order to reach solid tumor cells, a chemotherapeutic agent must overcome potentially long diffusion distances, closely packed tumor cells, and a dense fibrous stroma with a high interstitial pressure that impedes extravasation (Burrows and Thorpe, *Pharmacol. Ther.* 64:155–174 (1994)).

In addition, where the tumor vasculature is targeted, the killing of all target cells may not be required, since partial denudation of the endothelium can lead to the formation of an occlusive thrombus halting the blood flow through the entirety of the affected tumor vessel (Burrows and Thorpe, supra, 1994). Furthermore, unlike direct tumor targeting, there is an intrinsic amplification mechanism in tumor vasculature targeting. A single capillary loop can supply nutrients to up to 100 tumor cells, each of which is critically dependent on the blood supply (Denekamp, *Cancer Metast. Rev.* 9:267–282 (1990); Folkman, supra, 1997).

Endothelial cells in a tumor also are unlikely to lose a cell surface target receptor or develop a drug resistance phenotype, as can develop through mutation and clonal evolution of tumor cells, because endothelial cells are genetically stable despite their high proliferation rates (Burrows and Thorpe, supra, 1994; Folkman, supra, 1995; Folkman, supra, 1997). In this regard, it has been long recognized by medical oncologists that, while tumors treated with chemotherapeutic agents commonly develop drug resistance, normal tissues such as bone marrow do not develop such resistance. Thus, toxicity to normal tissues such as chemotherapy induced myelosuppression continues to occur during a treatment, even after tumor cells have become drug resistant. Since the endothelial cells in blood vessels supplying a tumor are nontumor cells, it is expected that they will not develop resistance to chemotherapeutic agents, in a manner analogous to bone marrow cells. In fact, drug resistance has not been observed during long term anti-angiogenic therapy in either experimental animals or in clinical trials (Folkman, supra, 1997).

Linking of a moiety larger than an agent such as a drug or other organic or biologic molecule to a tumor homing molecule for the purpose of directing homing of the moiety to the selected tumor is exemplified by expressing an RGD-containing peptide on a phage, wherein the peptide directed homing of the phage to breast tumor vasculature (Example IV). These results indicate that a tumor homing molecule of the invention can be linked to other moieties including, for example, a chambered microdevice or a liposome or a cell such as a white blood cell (WBC), which can be a cytotoxic T cell or a killer cell, wherein upon administration of the tumor homing molecule/WBC conjugate, the molecule directs homing of the WBC to the tumor, where the WBC can exert its effector function.

The linking of a moiety to a tumor homing molecule can result in the molecule directing homing of the linked moiety to a tumor. For example, the linking of a brain homing peptide to a RBC directed homing of the RBC to brain (see U.S. Pat. No. 5,622,699; Pasqualini and Ruoslahti, supra, 1996). This result indicates that a tumor homing molecule of the invention also can be linked to cell type or to a physical, chemical or biological delivery system such as a liposome or other encapsulating device, which can contain an agent such as drug, in order to direct the cell type or the delivery system to a selected tumor. For example, a tumor homing molecule identified by in vivo panning can be linked to a white blood cell (WBC) such as a cytotoxic T cell or a killer cell, wherein upon administration of the tumor homing molecule/WBC conjugate, the molecule directs homing of the WBC to the tumor, where the WBC can exert its effector function. Similarly, a tumor homing molecule can be linked to a liposome or to a chambered microdevice comprising, for example, a permeable or semipermeable membrane, wherein an agent such as a drug to be delivered to a selected tumor is contained within the liposome or microdevice. Such compositions also can be useful, for example, for delivering a nucleic acid molecule to a tumor cells, thereby providing a means for performing in vivo targeted gene therapy.

In one embodiment, a tumor homing molecule is linked to a moiety that is detectable external to the subject, thereby providing a composition useful to perform an in vivo diagnostic imaging study. For example, in vivo imaging using a detectably labeled tumor homing peptide can identify the presence of a tumor in a subject. For such studies, a moiety such as a gamma ray emitting radionuclide, for example, indium-111 or technitium-99, can be linked to the tumor homing molecule and, following administration to a subject, can be detected using a solid scintillation detector. Similarly, a positron emitting radionuclide such as carbon-11 or a paramagnetic spin label such as carbon-13 can be linked to the molecule and, following administration to a subject, the localization of the moiety/molecule can be detected using positron emission transaxial tomography or magnetic resonance imaging, respectively. Such methods can identify a primary tumor as well as a metastatic lesion, which may not be detectable using other methods. Having identified the presence of a cancer in a subject, in another embodiment of the invention, the tumor homing molecule is linked to a cytotoxic agent such as ricin or a cancer chemotherapeutic agent such as doxorubicin in order to direct the moiety to the tumor or can be linked to a chambered microdevice, which can contain a chemotherapeutic drug or other cytotoxic agent. Use of such a composition provides a means to selectively killing of the tumor, while substantially sparing normal tissues in a cancer patient and, therefore, the conjugates of the invention provide useful medicaments for diagnosing or treating a cancer patient.

The skilled artisan would recognize that various tumor homing molecules can selectively home only to a tumor or can selectively home to a tumor and to a family of selected organs, including, in some cases, the normal tissue counterpart to the tumor. Thus, the artisan would select a tumor homing peptide for administration to a subject based on the procedure being performed. For example, a tumor homing molecule that homes only to a tumor can be useful for directing a therapy to the tumor. In comparison, a tumor homing molecule that selectively homes not only to the tumor, but also to one or more normal organs or tissues, can be used in an imaging method, whereby homing to an organ or tissue other than the tumor provides an internal imaging control. Such an internal control can be useful, for example, for detecting a change in the size of a tumor in response to a treatment, since the normal organ is not expected to change in size and, therefore, can be compared with the tumor size.

Tumor homing peptides, which are identified by in vivo panning, can be synthesized in required quantities using routine methods of solid state peptide synthesis or can be purchased from commercial sources (for example, Anaspec; San Jose Calif.). and a desired moiety can be linked to the molecule. Several methods useful for linking a moiety to a molecule are known in the art, depending on the particular chemical characteristics of the molecule. For example, methods of linking haptens to carrier proteins as used routinely in the field of applied immunology (see, for example, Harlow and Lane, supra, 1988; Hermanson, supra, 1996).

It is recognized that, in some cases, a drug can lose cytotoxic efficacy upon conjugation or derivatization depending, for example, on the conjugation procedure or the chemical group utilized (Hurwitz et al., *Cancer Res.* 35:1175–1181 (1975); Trail et al., *Science* 261;212–215 (1993); Nagy et al., *Proc. Natl. Acad. Sci. USA* 93:7269–7273 (1996)). Moreover, it is recognized that a phage that yields a tumor homing peptide of the invention displays as any as five of the peptides. Thus, there is a possibility that the affinity of an individual peptide is too low for effective tumor homing and that multivalent, rather than univalent, peptide conjugates must be used. However, as disclosed herein, doxorubicin maintained cytotoxic activity when used as a conjugate with tumor homing peptides (see Example VII), thus allaying the potential concerns discussed above.

A moiety such as a therapeutic or diagnostic agent can be conjugated to a tumor homing peptide using, for example, carbodiimide conjugation (Bauminger and Wilchek, *Meth. Enzymol.* 70:151–159 (1980), which is incorporated herein by reference). Carbodiimides comprise a group of compounds that have the general formula R—N=C=N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies.

The water soluble carbodiimide, 1-ethyl-3-(3-dimethylaminopropyl)carbodiimide (EDC) is particularly useful for conjugating a moiety to a tumor homing peptide and was used to conjugate doxorubicin to tumor homing peptides (Example VI). The conjugation of doxorubicin and a tumor homing peptide requires the presence of an amino group, which is provided by doxorubicin, and a carboxyl group, which is provided by the peptide. EDC coupling of doxorubicin to the CNGRC (SEQ ID NO: 8) peptide was performed using a 1:1 molar ratio of the peptide (carboxyl groups) to obtain a doxorubicin/CNGRC (SEQ ID NO: 8; see Example VI).

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger and Wilchek, supra, 1980).

Other methods for conjugating a moiety to a tumor homing molecule also can be used. For example, sodium periodate oxidation followed by reductive alkylation of appropriate reactants can be used, as can glutaraldehyde crosslinking. However, it is recognized that, regardless of which method of producing a conjugate of the invention is selected, a determination must be made that the tumor homing molecule maintains its targeting ability and that the moiety maintains its relevant function. Methods as disclosed in Example VII or otherwise known in the art can confirm the activity of the moiety/tumor homing molecule conjugate.

The yield of moiety/tumor homing molecule conjugate formed is determined using routine methods. For example, HPLC or capillary electrophoresis or other qualitative or quantitative method can be used (see, for example, Liu et al., *J. Chromatogr.* 735:357–366 (1996); Rose et al., *J. Chromatogr.* 425:419–412 (1988), each of which is incorporated herein by reference; see, also, Example V). In particular, the skilled artisan will recognize that the choice of a method for determining yield of a conjugation reaction depends, in part, on the physical and chemical characteristics of the specific moiety and tumor homing molecule. Following conjugation, the reaction products are desalted to remove any free peptide and free drug.

When administered to a subject, the tumor homing molecule/moiety conjugate is administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art would know that a pharmaceutical composition containing a tumor homing molecule can be administered to a subject by various routes including, for example, orally or parenterally, such as intravenously. The composition can be administered by injection or by intubation. The pharmaceutical composition also can be a tumor homing molecule linked to liposomes or other polymer matrices, which can have incorporated therein, for example, a drug such as a chemotherapeutic agent (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

For the diagnostic or therapeutic methods disclosed herein, an effective amount of the tumor homing molecule/moiety conjugate must be administered to the subject. As used herein, the term "effective amount" means the amount of the conjugate that produces the desired effect. An effective amount often will depend on the moiety linked to the tumor homing molecule. Thus, a lesser amount of a radiolabeled molecule can be required for imaging as compared to the amount of a drug/molecule conjugate administered for therapeutic purposes. An effective amount of a particular molecule/moiety for a specific purpose can be determined using methods well known to those in the art.

The route of administration of a tumor homing molecule will depend, in part, on the chemical structure of the molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). Such modifications can be performed on peptides identified by in vivo panning. In addition, methods for preparing libraries of peptidomimetics, which can contain D-amino acids, other non-naturally occurring amino acids, or chemically modified amino acids; or can be organic molecules that mimic the structure of peptide; or can be peptoids such as vinylogous peptoids, are known in the art and can be used to identify molecules that home to a tumor and are stable for oral administration.

Tumor homing molecules obtained using the methods disclosed herein also can be useful for identifying a target molecule such as a cell surface receptor or a ligand for a receptor, which is recognized by the tumor homing peptide, or for substantially isolating the target molecule. For example, a tumor homing peptide can be linked to a solid support such as a chromatography matrix. The linked peptide then can be used for affinity chromatography by passing an appropriately processed sample of a tumor over the column in order to bind a particular target molecule. The target molecule, which forms a complex with the tumor homing molecule, then can be eluted from the column and collected in a substantially isolated form. The substantially isolated target molecule then can be characterized using well known methods. A tumor homing peptide also can be linked to a detectable moiety such as a radionuclide, a fluorescent molecule, an enzyme or biotin and can be used, for example, to screen a sample in order to detect the presence of the target molecule in a tumor or to follow the target molecule during various isolation steps.

It follows that, upon identifying the presence of a target molecule in a tumor sample, the skilled artisan readily can obtain the target molecule in a substantially isolated form. For example, the sample containing the target molecule can be passed over a column containing attached thereto the relevant tumor homing molecule, thereby providing a means to obtain the target molecule in substantially isolated form. Thus, the invention further provides a substantially isolated target molecule, which specifically binds a tumor homing molecule and which can be obtained using the methods disclosed herein.

The methods of the present invention were used to identify tumor homing peptides, which can selectively home to various tumors. It should be recognized that cysteine residues were included in some peptides such that cyclization of the peptides could be effected. In fact, the peptides containing at least two cysteine residues cyclize spontaneously. However, such cyclic peptides also can be active when present in a linear form (see, for example, Koivunen et al., supra, 1993) and, as disclosed herein, a linear peptide, NGRAHA (SEQ ID NO: 6), also was useful as tumor homing molecule (Example VII; see, also, Table 1). Thus, in some cases one or more cysteine residues in the peptides disclosed herein or otherwise identified as tumor homing peptides can be deleted without significantly affecting the tumor homing activity of the peptide. Methods for determining the necessity of a cysteine residue or of amino acid residues N-terminal or C-terminal to a cysteine residue for tumor homing activity of a peptide of the invention are routine and well known in the art.

A tumor homing peptide is useful, for example, for targeting a desired moiety to the selected tumor as discussed above. In addition, a tumor homing peptide can be used to identify the presence of a target molecule in a sample. As used herein, the term "sample" is used in its broadest sense to mean a cell, tissue, organ or portion thereof, including a tumor, that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which a tumor homing molecule binds.

A tumor homing peptide such as a breast tumor homing peptide can be used to identify the target molecule expressed in a breast tumor. For example, a breast tumor homing peptide can be attached to a matrix such as a chromatography matrix to produce a peptide affinity matrix. A homogenized sample of a breast tumor can be applied to the peptide-affinity matrix under conditions that allow specific binding of the target molecule to the tumor homing peptide (see, for example, Deutshcer, *Meth. Enzymol.*, Guide to Protein Purification (Academic Press, Inc., ed. M. P. Deutscher, 1990), Vol. 182, which is incorporated herein by reference; see, for example, pages 357–379). Unbound and nonspecifically bound material can be removed and the specifically bound breast tumor-derived target molecule can be isolated in substantially purified form. The presence or absence of the target molecule in normal breast tissue also can be determined. Such an analysis can provide insight into methods of treating the tumor.

As disclosed herein, a target molecule, which specifically binds a tumor homing molecule, can be identified by contacting a sample of a tumor with such a tumor homing molecule and identifying a target molecule bound by the tumor homing molecule. In parallel, the tumor homing molecule is contacted with a sample of a nontumor tissue corresponding to the tumor. The presence of the target molecule in the tumor sample can be identified by determining that the tumor homing molecule does not bind to a component of the corresponding nontumor tissue sample. Thus, the invention provides methods for identifying the presence of a target molecule, which is expressed in a tumor and specifically bound by a tumor homing molecule.

Since numerous tumor homing peptides containing the NGR motif have been identified, for example, a tumor homing peptide comprising an NGR sequence can be used to isolate the NGR receptor. Thus, an NGR tumor homing peptide can be linked to a solid matrix and an appropriately processed sample of a tumor, which specifically binds the NGR peptide, can be passed over the NGR peptide-matrix. The NGR receptor, which is the target molecule for the NGR tumor homing peptide, then can be obtained in a substantially isolated form. When used in reference to a target molecule, the term "substantially isolated" means that the target molecule comprises at least 30% of the total protein present, although the target molecule can comprise at least 50% of the total protein, or 80% of the total protein, or 90% or 95% of the total protein, or more. A method such as gel electrophoresis and silver staining can be used to determine the relative amount of a target molecule in a sample, following a purification protocol, and, therefore, can be used to identify a substantially isolated target molecule.

The skilled artisan will recognize that a substantially isolated target molecule can be used as an immunogen to obtain antibodies that specifically bind the target molecule. As used herein, the term "antibody" is used in its broadest sense to include polyclonal and monoclonal antibodies, as well as antigen binding fragments of such antibodies. With regard to an antibody of the invention, which specifically binds a target molecule targeted by a tumor homing molecule, the term "antigen" means the target molecule polypeptide or peptide portion thereof. An antibody or antigen binding fragment of an antibody that binds a target molecule is characterized by having specific binding activity for the target molecule or a peptide portion thereof of at least about $1 \times 10^5$ $M^{-1}$, preferably at least about $1 \times 10^6$ $M^{-1}$, and more preferably at least about $1 \times 10^8$ $M^{-1}$. Thus, Fab, F(ab')$_2$, Fd and Fv fragments of the antibody, which retain specific binding activity for a target molecule, which is expressed by angiogenic vasculature, are included within the definition of an antibody.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Hilyard et al., *Protein Engineering: A practical approach* (IRL Press 1992); Borrabeck, *Antibody Engineering*, 2d ed. (Oxford University Press 1995); each of which is incorporated herein by reference; see, also, Harlow and Lane, supra, 1988).

Antibodies that specifically bind a target molecule of the invention can be raised using as an immunogen a substantially isolated target molecule, which can be obtained as disclosed herein, or a peptide portion of the target molecule, which can be obtained, for example, by enzymatic degradation of the target molecule and gel purification. A non-immunogenic peptide portion of a target molecule can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art and described, for example, by Harlow and Lane, supra, 1988).

Particularly useful antibodies of the invention are those that bind to the tumor homing molecule binding site on the target molecule, such antibodies being readily identifiable by detecting competitive inhibition of binding of the antibody and the particular tumor homing molecule that binds to the target molecule. Conversely, antibodies that bind to an epitope of the target molecule that is not involved in binding the tumor homing molecule also are valuable, since such antibodies, which, themselves, can be "tumor homing molecules," can be bind to target molecules having another tumor homing molecule bound thereto.

An antibody that specifically binds a target molecule, for example, the NGR receptor, is useful for determining the presence or level of the target molecule in a tissue sample, which can be a lysate or a histological section. The identification of the presence or level of the target molecule in the sample can be made using well known immunoassay and immunohistochemical methods (Harlow and Lane, supra, 1988). An antibody specific for a target molecule also can be used to substantially isolate the target molecule from a sample. In addition, an antibody of the invention can be used in a screening assay to identify, for example, peptidomimetics of a tumor homing molecule that bind to the target molecule or as a tool for tumor targeting.

Upon obtaining a target molecule, which, due to the nature of a tumor homing molecule, is expressed in angiogenic vasculature, for example, the angiogenic vasculature in a tumor, the naturally occurring ligand for the target molecule, where it exists, can be identified. Methods for identifying a ligand for such a target molecule, which is akin to an "orphan receptor," are well known in the art and include, for example, screening biological samples to identify the ligand. A convenient screening assay to identify a natural ligand for the target molecule can utilize the ability of a putative natural ligand to competitively inhibit the binding to the target molecule of a tumor homing molecule that specifically binds the target molecule, for example, the tumor homing peptide used to obtain the substantially isolated target molecule.

A screening assay comprising a competitive binding assay for the target molecule and, for example, the natural ligand for the target molecule or a tumor homing peptide that specifically binds the target molecule, also provides a means to identify peptidomimetics of a tumor homing molecule. As discussed above, such peptidomimetics can provide advantages over tumor homing peptides in that they can be small, relatively stable for storage, conveniently produced in suitable quantities, and capable of being administered orally. A peptidomimetic of a tumor homing peptide can be identified by screening libraries of peptidomimetics in a competitive binding assay as described above.

The disclosed in vivo panning method can be used to detect four different kinds of target molecules in tumors. First, because tumor vasculature undergoes active angiogenesis, target molecules that are characteristic of angiogenic vasculature, in general, or angiogenic tumor vasculature, in particular, can be identified. Second, vascular target molecules that are characteristic of the tissue of origin of the tumor can be identified. Third, target molecules that are expressed in the vasculature of a particular type of tumor can be identified. Fourth, tumor stroma or tumor cell target molecules can be identified due to the fenestrated nature of tumor vasculature, which allows the potential tumor homing molecules to leave the circulation and contact the tumor parenchyma.

As further disclosed herein, some, but not all, tumor homing molecules also can home to angiogenic vasculature that is not contained within a tumor. For example, tumor homing molecules containing either the RGD motif or the GSL motif specifically homed to retinal neovasculature (Smith et al., Invest. Ophthamol. Vis. Sci. 35:101–111 (1994), which is incorporated herein by reference), whereas tumor homing peptides containing the NGR motif did not accumulate substantially to this angiogenic vasculature. Thus, the present invention also provides peptides that home to nontumor angiogenic vasculature. Furthermore, these results indicate that tumor vasculature expressing target molecules that are not substantially expressed by other kinds of angiogenic vasculature. Thus, the present invention provides a means to identify target molecules expressed specifically by angiogenic vasculature present in a tumor, as well as for target molecules expressed by angiogenic vasculature not associated with a tumor. Methods as disclosed herein can be used to distinguish such homing peptides and to isolate the various target molecules.

As an alternative to using a tumor sample to obtain the target molecule, extracts of cultured tumor cells or endothelial cells, depending on which cell type expresses the target molecule, can be used as the starting material in order to enhance the concentration of the target molecule in the sample. It is recognized, however, that the characteristics of such cells can change upon adaptation to tissue culture. Thus, care must be exercised if such a preselection step is attempted. The presence of the target molecule can be established, for example, by using phage binding and cell attachment assays (see, for example, Barry et al., supra, 1996).

A cell line expressing a particular target molecule can be identified and surface iodination of the cells can be used to label the target molecule. The cells then can be extracted, for example, with octylglucoside and the extract can be fractionated by affinity chromatography using a tumor homing peptide (see Tables 1 and 2) coupled to a matrix such as SEPHAROSE (see Hermanson, supra, 1996). The purified target molecule can be microsequenced and antibodies can be prepared. If desired, oligonucleotide probes can be prepared and used to isolate cDNA clones encoding the target molecule. Alternatively, an anti-target molecule antibody can be used to isolate a cDNA clone from an expression library (see Argraves et al., J. Cell Biol. 105:1183–1190 (1987), which is incorporated herein by reference).

As an alternative to isolating the target molecule, a nucleic acid encoding the target molecule can be isolated using a mammalian cell expression cloning system such as the COS cell system. An appropriate library can be prepared, for example, using mRNA from primary tumor cells. The nucleic acids can be cloned into the pcDNAIII vector (Invitrogen), for example. Cells expressing a cDNA for the target molecule can be selected by binding to the tumor homing peptide. Purified phage can be used as the carrier of the peptide and can be attached to magnetic beads coated, for example, with anti-M13 antibodies (Pharmacia Biotech; Piscataway N.J.). Cells that bind to the peptide coating can be recovered using a magnet and the plasmids can be isolated. The recovered plasmid preparations then can be divided into pools and examined in COS cell transfections. The procedure can be repeated until single plasmids are obtained that can confer upon the COS cells the ability to bind the tumor homing peptide.

The following examples are intended to illustrate but not limit the present invention.

EXAMPLE I

In Vivo Panning

This example demonstrates methods for preparing a phage library and screening the library using in vivo panning to identify phage expressing peptides that home to a tumor.

A. Preparation of Phage Libraries

Phage display libraries were constructed using the fuse 5 vector as described by Koivunen et al. (supra, 1995; Koivunen et al., supra, 1994b). Libraries encoding peptides designated $CX_5C$ (SEQ ID NO: 9), $CX_6C$ (SEQ ID NO: 10), $CX_7C$ (SEQ ID NO: 11) and $CX_3CX_3CX_3C$ (SEQ ID NO: 12) were prepared, where "C" indicates cysteine and "$X_N$" indicates the given number of individually selected amino acids. These libraries can display cyclic peptides when at least two cysteine residues are present in the peptide. In addition, a library that did not contain defined cysteine residues also was constructed. Such a library results in the production primarily of linear peptides, although cyclic peptides also can occur due to random probability.

A biased library based on the sequence CXXXNGRXX (SEQ ID NO: 13) also was constructed. Furthermore, in some cases the CXXXNGRXX (SEQ ID NO: 13) library was further biased by in the incorporation of cysteine residues flanking the NGR sequence, i.e., CXXCNGRCX (SEQ ID NO: 14; see Table 1).

The libraries containing the defined cysteine residues were generated using oligonucleotides constructed such that "C" was encoded by the codon TGT and "$X_N$" was encoded by NNK, where "N" is equal molar mixtures of A, C, G and T, and where "K" is equal molar mixtures of G and T. Thus, the peptide represented by $CX_5C$ (SEQ ID NO: 9) can be represented by an oligonucleotide having the sequence TGT (NNK)$_5$TGT (SEQ ID NO: 14). Oligonucleotides were made double stranded by 3 cycles of PCR amplification, purified and ligated to the nucleic acid encoding the gene III protein in the fuse 5 vector such that, upon expression, the peptide is present as a fusion protein at the N-terminus of the gene III protein.

The vectors were transfected by electroporation into MC1061 cells. Bacteria were cultured for 24 hr in the presence of 20 μg/ml tetracycline, then phage were collected from the supernatant by precipitation twice using polyethylene glycol. Each library contained about $5 \times 10^9$ to $5 \times 10^{14}$ transducing units (TU; individual recombinant phage).

B. In vivo Panning of Phage

Tumors were transplanted into mice as described in Examples II and III, below. A mixture of phage libraries containing $1 \times 10^9$ to $1 \times 10^{14}$ TU was diluted in 200 μl DMEM and injected into the tail vein of anesthetized mice (AVERTIN (0.015 ml/g); see U.S. Pat. No. 5,622,699; Pasqualini and Ruoslahti, supra, 1996). After 1–4 minutes, mice were snap frozen in liquid nitrogen. To recover the phage, carcasses were partially thawed at room temperature for 1 hr, tumors and control orqans were collected and weighed, then were ground in 1 ml DMEM-PI (DMEM containing protease inhibitors (PI); phenylmethylsulfonyl fluoride (PMSF; 1 mM), aprotinin (20 μg/ml), leupeptin (1 μg/ml)).

Alternatively, following introduction of a library into a mouse, circulation of the library is terminated by perfusion through the heart. Briefly, mice were anesthetized with AVERTIN, then the heart was exposed and a 0.4 mm needle connected through a 0.5 mm cannula to a 10 cc syringe was inserted into the left ventricle. An incision was made on the right atrium and 5 to 10 ml of DMEM was slowly administered, perfusing the whole body over about a 5 to 10 min period. Efficiency of the perfusion was monitored directly by histologic analysis.

Tumor and organ samples were washed 3 times with ice cold DMEM-PI containing 1% bovine serum albumin (BSA), then directly incubated with 1 ml K91-kan bacteria for 1 hr. Ten ml NZY medium containing 0.2 μg/ml tetracycline (NZY/tet) was added to;the bacterial culture, the mixture was incubated in a 37° C. shaker for 1 hr, then 10 μl or 100 μl aliquots were plated in agar plates containing 12.5 μg/ml tetracycline (tet/agar).

Individual colonies containing phage recovered from a tumor were grown for 16 hr in 5 ml NZY/tet. The bacterial cultures obtained from the individual colonies were pooled and the phage were purified and re-injected into mice as described above for a second round of in vivo panning. In general, a third round of panning also was performed. Phage DNA was purified from individual bacterial colonies obtained from the final round of in vivo panning and the DNA sequences encoding the peptides expressed by selected phage were determined (see Koivunen et al., supra, 1994b).

EXAMPLE II

Identification of Tumor Homing Peptides by In Vivo Panning Against a Breast Tumor This example demonstrates that in vivo panning can be performed against a breast tumor to identify tumor homing peptides that home to various tumors.

Human 435 breast carcinoma cells (Price et al., *Cancer Res.* 50:717–721 (1990)) were inoculated into the mammary fat pad of nude mice. When the tumors attained a diameter of about 1 cm, either a phage targeting experiment was performed, in which phage expressing a specific peptide were administered to the tumor bearing mouse, or in vivo panning was performed.

The breast tumor bearing mice were injected with $1 \times 10^9$ phage expressing a library of $CX_3CX_3CX_3C$ (SEQ ID NO: 12) peptides, where $X_3$ indicates three groups of independently selected, random amino acids. The phage were allowed to circulate for 4 min, then the mice were anesthetized, snap frozen in liquid nitrogen while under anesthesia, and the tumor was removed. Phage were isolated from the tumor and subjected to two additional rounds of in vivo panning.

Following the third round of panning, phage were quantitated and the peptide sequences expressed by the cloned phage were determined. The cloned phage expressed various different peptides, including those shown in Table 1. Similarly, $CX_7C$ (SEQ ID NO: 11) and $CX_5C$ (SEQ ID NO: 9) libraries were screened and breast tumor homing peptides were identified (Table 1). These results demonstrate that in vivo panning against a breast tumor can identify tumor homing molecules.

EXAMPLE III

In Vivo Targeting of a Phage Expressing an RGD Peptide to a Tumor

Human 435 breast carcinoma cells were inoculated into the mammary fat pad of nude mice. When the tumors attained a diameter of about 1 cm, phage expressing a specific RGD-containing peptide were administered to the tumor bearing mouse. Similar results

TABLE 1

| PEPTIDES FROM PHAGE RECOVERED FROM HUMAN BREAST CANCER | | | | | |
|---|---|---|---|---|---|
| CGRECPRLCQSSC | (2*) | CNGRCVSGCAGRC | (3) | | |
| CGEACGGQCALPC | (20) | IWSGYGVYW | (21) | | |
| PSCAYMCIT | (22) | WESLYFPRE | (23) | | |
| SKVLYYNWE | (24) | CGLMCQGACFDVC | (25) | | |
| CERACRNLCREGC | (26) | CPRGCLAVCVSQC | (27) | | |
| CKVCNGRCCG | (28) | CEMCNGRCMG | (29) | CPLCNGRCAL | (30) |
| CPTCNGRCVR | (31) | CGVCNGRCGL | (32) | CEQCNGRCGQ | (33) |
| CRNCNGRCEG | (34) | CVLCNGRCWS | (35) | CVTCNGRCRV | (36) |
| CTECNGRCQL | (37) | CRTCNGRCLE | (38) | CETCNGRCVG | (39) |
| CAVCNGRCGF | (40) | CRDLNGRKVM | (41) | CSCCNGRCGD | (42) |
| CWGCNGRCRM | (43) | CPLCNGRCAR | (44) | CKSCNGRCLA | (45) |

TABLE 1-continued

PEPTIDES FROM PHAGE RECOVERED FROM HUMAN BREAST CANCER

| | | | | | |
|---|---|---|---|---|---|
| CVPCNGRCHE | (46) | CQSCNGRCVR | (47) | CRTCNGRCQV | (48) |
| CVQCNGRCAL | (49) | CRCCNGRCSP | (50) | CASNNGRVVL | (51) |
| CGRCNGRCLL | (52) | CWLCNGRCGR | (53) | CSKCNGRCGH | (54) |
| CVWCNGRCGL | (55) | CIRCNGRCSV | (56) | CGECNGRCVE | (57) |
| CEGVNGRRLR | (58) | CLSCNGRCPS | (59) | CEVCNGRCAL | (60) |
| CGSLVRC | (5) | GRSQMQI | (61) | HHTRFVS | (62) |
| SKGLRHR | (63) | VASVSVA | (64) | WRVLAAF | (65) |
| KMGPKVW | (66) | IFSGSRE | (67) | SPGSWTW | (68) |
| NPRWFWD | (69) | GRWYKWA | (70) | IKARASP | (71) |
| SGWCYRC | (72) | ALVGLMR | (73) | LWAEMTG | (74) |
| CWSGVDC | (75) | DTLRLRI | (76) | SKSSGVS | (77) |
| IVADYQR | (78) | VWRTGHL | (79) | VVDRFPD | (80) |
| LSMFTRP | (81) | GLPVKWS | (82) | IMYPGWL | (83) |
| CVMVRDGDC | (84) | CVRIRPC | (85) | CQLAAVC | (86) |
| CGVGSSC | (87) | CVSGPRC | (88) | CGLSDSC | (89) |
| CGEGHPC | (90) | CYTADPC | (91) | CELSLISKC | (92) |
| CPEHRSLVC | (93) | CLVVHEAAC | (94) | CYVELHC | (95) |
| CWRKFYC | (96) | CFWPNRC | (97) | CYSYFLAC | (98) |
| CPRGSRC | (99) | CRLGIAC | (100) | CDDSWKC | (101) |
| CAQLLQVSC | (102) | CYPADPC | (103) | CKALSQAC | (104) |
| CTDYVRC | (105) | CGETMRC | (106) | | |

*numbers in parentheses indicate SEQ ID NO:.

to those discussed below also were obtained with nude mice bearing tumors formed by implantation of human melanoma C8161 cells or by implantation of mouse B16 melanoma cells.

$1 \times 10^9$ phage expressing the RGD-containing peptide, CDCRGDCFC (SEQ ID NO: 1; see, Koivunen et al., supra, 1995) or control (insertless) phage were injected intravenously (iv) into the mice and allowed to circulate for 4 min. The mice then were snap frozen or perfused through the heart while under anesthesia, and various organs, including tumor, brain and kidney, were removed and the phage present in the organs was quantitated (see U.S. Pat. No. 5,622,699; Pasqualini and Ruoslahti, supra, 1996).

Approximately 2–3 times more phage expressing the CDCRGDCFC (SEQ ID NO: 1) peptide were detected in the breast tumor as compared to brain and kidney, indicating the CDCRGDCFC (SEQ ID NO: 1; RGD phage) peptide resulted in selective homing of the phage to the breast tumor. In a parallel study, unselected phage, which express various, diverse peptides, were injected into tumor-bearing mice and various organs were examined for the presence of phage. Far more phage were present in kidney and, to a lesser extent, brain, as compared to the tumor. Thus, the 80-fold more RGD-expressing phage than unselected phage concentrated in the tumor. These results indicate that phage expressing the RGD-containing peptide home to a tumor, possibly due to the expression of the $\alpha_v\beta_3$ integrin on blood vessels forming in the tumor.

Specificity of the breast tumor homing peptide was demonstrated by competition experiments, in which coinjection of 500 μg free peptide, ACDCRGDCFCG (SEQ ID NO: 16; see Pasqualini et al., supra, 1997) with the phage expressing the tumor homing peptide reduced the amount of phage in the tumor by about tenfold, whereas coinjection with the inactive control peptide, GRGESP (SEQ ID NO: 17) essentially had no effect. These results demonstrate that phage displaying a peptide that can bind to an integrin expressed on angiogenic vasculature can selectively home in vivo to an organ or tissue such as a tumor containing such vasculature.

EXAMPLE IV

Immunohistologic Analysis of Tumor Homing Peptides

This example provides a method of identifying the localization of tumor homing molecules by immunohistologic examination.

Localization of phage expressing a tumor homing peptide was identified by immunochemical methods in histologic sections obtained either, 5 min or 24 hr after administration of phage expressing a tumor homing peptide ("peptide-phage") to a tumor bearing mouse (FIG. 1). For samples obtained 5 min following administration of the peptide-phage, mice were perfused with DMEM and various organs, including the tumor, were removed and fixed in Bouin's solution. For samples obtained at 24 hr, no peptide-phage remains in the circulation and, therefore, perfusion was not required. Histologic sections were prepared and reacted with anti-M13 (phage) antibodies (Pharmacia Biotech; see U.S. Pat. No. 5,622,699; Pasqualini and Ruoslahti, supra, 1996). Visualization of the bound anti-M13 antibody was performed using a peroxidase-conjugated second antibody (Sigma; St. Louis Mo.) according to the manufacturer's instructions.

As discussed in Example III, phage expressing the tumor homing peptide, CDCRGDCFC (SEQ ID NO: 1; "RGD phage), were administered intravenously to mice bearing the breast tumor. In addition, the RGD phage were administered to mice bearing a mouse melanoma or a human Kaposi's sarcoma. Circulation of the phage was terminated and mice were sacrificed as described above and samples of the tumor and of skin adjacent to the tumor, brain, kidney, lung and liver were collected. Immunohistochemical staining for the phage showed accumulation of the RGD phage in the blood vessels present in the breast tumor as well as in the melanoma and the Kaposi's sarcoma, whereas little or no staining was observed in the control organs.

Similar experiments were performed using phage expressing the tumor homing peptide, CNGRCVSG-CAGRC (SEQ ID NO: 3; "NGR phage"), which was identified by in vivo panning against a tumor formed by the MDA-MB-435 breast carcinoma. In these experiments, NGR phage or control phage, which do not express a peptide, were administered to mice bearing tumors formed by the MDA-MB-435 breast carcinoma or by a human SLK Kaposi's sarcoma xenograft, then the mice were sacrificed as described above and tumors were collected as well as control organs, including brain, lymph node, kidney, pancreas, uterus, mammary fat pad, lung, intestine, skin, skeletal muscle, heart and epithelium of the renal calices, bladder and ureter (see FIG. 1). Histological samples were prepared and examined by immunostaining as described above.

Figure 1D:
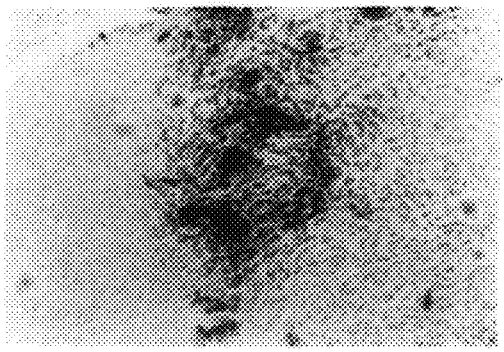
Figure 1E:
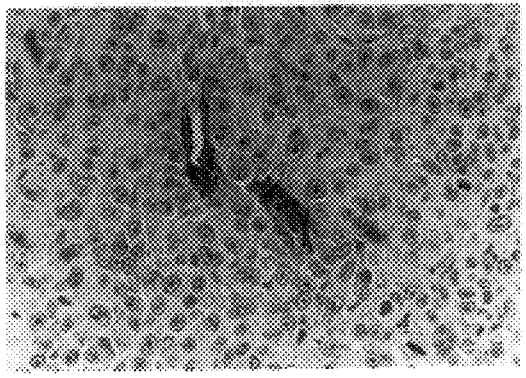
Figure 1H:
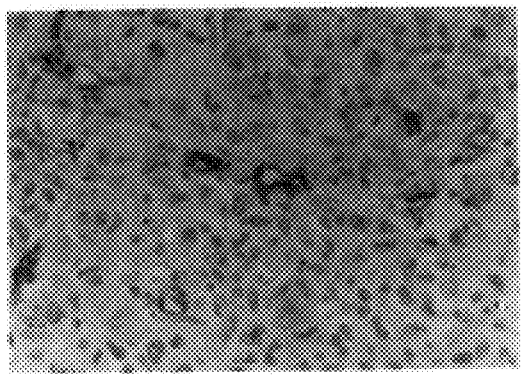
Figure 1F:
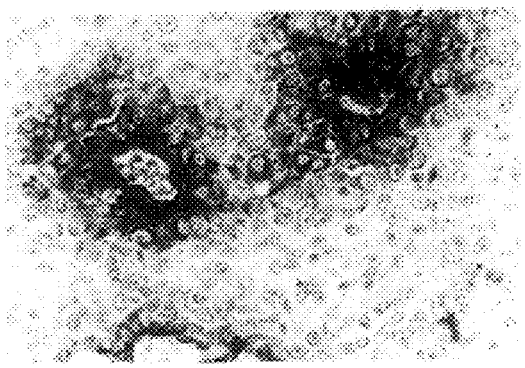
Figure 1I:
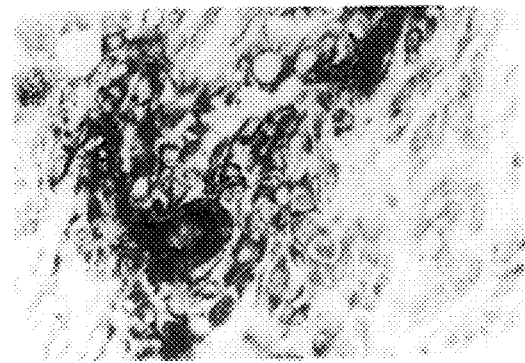
Figure 1G:
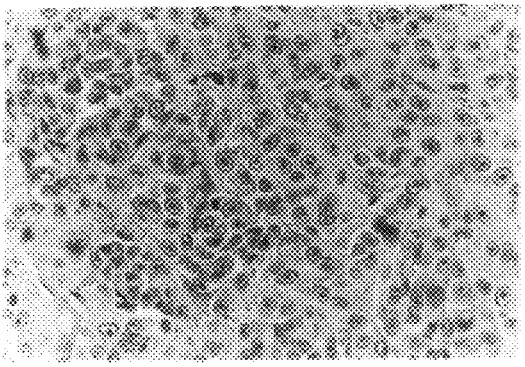
Figure 1J:
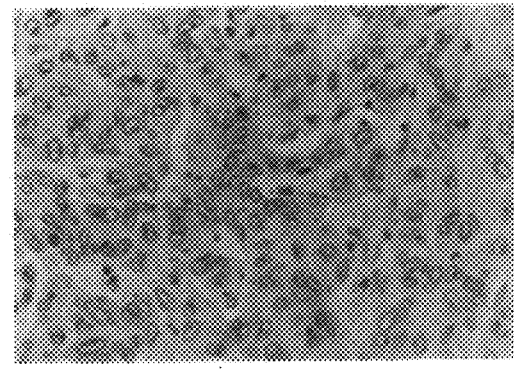
Figure 1K:
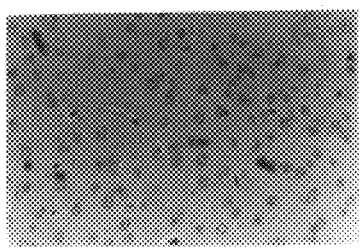
Figure 1L:
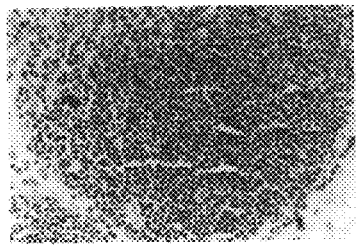
Figure 1M:
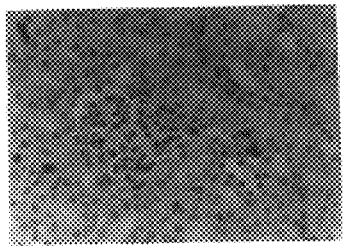
Figure 1N:
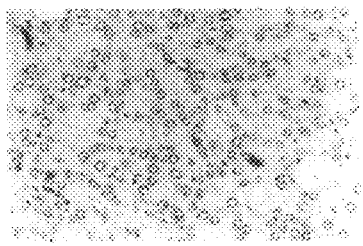
Figure 1O:
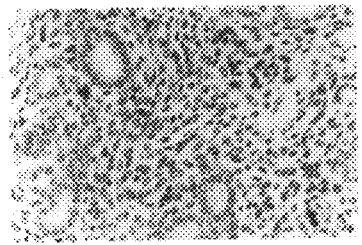
Figure 1P:
Figure 1Q:
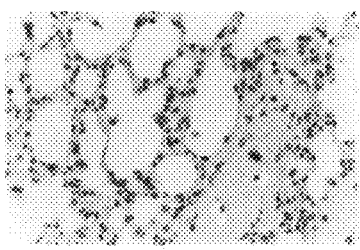
Figure 1R:
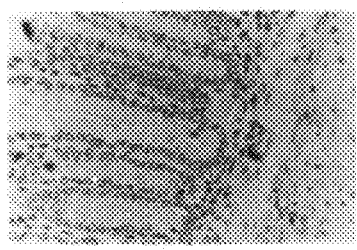
Figure 1S:
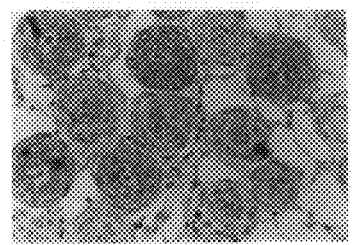
Figure 1T:
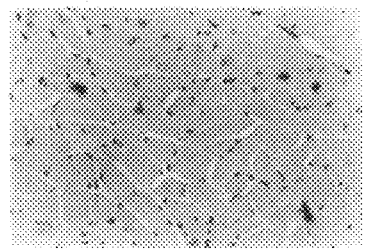
Figure 1U:
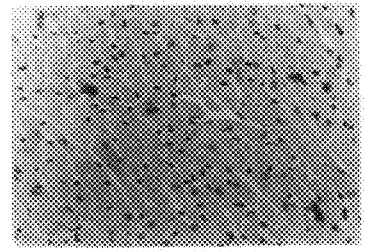
Figure 1V:
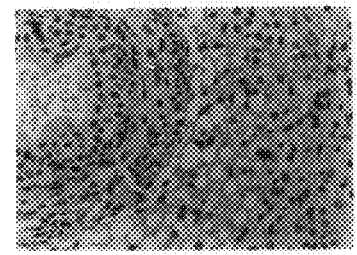

In samples obtained from mice sacrificed 4 min after administration of the NGR phage, immunostaining of the vasculature of both the breast tumor (FIG. 1E) and the Kaposi's sarcoma (FIG. 1H) was observed. Very little or no staining was observed in the endothelium of the these tumors in mice administered an insertless control phage (FIGS. 1G and 1J, respectively). In the samples obtained from mice sacrificed 24 hr after administration of the NGR phage, staining of the tumor samples appeared to have spread outside of the vessels, into the breast tumor parenchyma (FIGS. 1B and 1F) and the Kaposi's sarcoma parenchyma (FIGS. 1D and 1I). Again, little or no staining was observed in samples prepared from these tumors in mice administered the insertless control phage (FIGS. A and C, respectively). In addition, little or no staining was observed in various control organs in mice administered the NGR phage (FIGS. 1K to 1V).

In other experiments, similar results were obtained following administration of phage expressing the NGR tumor homing peptides, NGRAHA (SEQ ID NO: 6) or CVLN-GRMEC (SEQ ID NO: 7), to tumor bearing mice. Also, as discussed below, similar results were obtained using phage expressing the GSL tumor homing peptide, CLSGSLSC (SEQ ID NO: 4), which was identified by in vivo panning of a melanoma (see Example V, below).

These results demonstrate that tumor homing peptides selectively home to tumors, particularly to the vasculature in the tumors and that tumor homing peptides identified, for example, by in vivo panning against a breast carcinoma also selectively home to other tumors, including Kaposi's sarcoma and melanoma. In addition, these results demonstrate that immunohistochemical analysis provides a convenient assay for identifying the localization of phage expressing tumor homing peptides.

EXAMPLE V

Identification of Tumor Homing Peptides by In Vivo Panning Against a Melanoma Tumor The general applicability of the in vivo panning method to identify tumor homing peptides was examined by performing in vivo panning against an implanted mouse melanoma tumor.

Mice bearing a melanoma were produced by implantation of B16B15b mouse melanoma cells, which produce highly vascularized tumors. B16B15b mouse melanoma cells were injected subcutaneously into the mammary fat pad of nude mice (2 months old) and tumors were allowed to grow until the diameter was about 1 cm. In vivo panning was performed as disclosed above. Approximately $1 \times 10^{12}$ transducing units of phage expressing the $CX_5C$ (SEQ ID NO: 9), $CX_6C$ (SEQ ID NO: 10) or $CX_7C$ (SEQ ID NO: 11) library were injected, iv, and allowed to circulate for 4 min. Mice then were snap frozen in liquid nitrogen or perfused through the heart while under anesthesia, tumor tissue and brain (control organ) were removed, and phage were isolated as described above. Three rounds of in vivo panning were performed.

The amino acid sequences were determined for the inserts in 89 cloned phage recovered from the B16B15b tumors. The peptides expressed by these phage were represented by two predominant sequences, CLSGSLSC (SEQ ID NO: 4; 52% of the clones sequenced) and WGTGLC (SEQ ID NO: 18; 25% of the clones; see Table 2). Reinfection of phage expressing one of the selected peptides resulted in approximately three-fold enrichment of phage homing to the tumor relative to brain.

TABLE 2

PEPTIDES FROM PHAGE RECOVERED FROM MOUSE B16B15b MELANOMA

| CLSGSLSC | (4*) | GICKDDWCQ | (107) | TSCDPSLCE | (108) |
|---|---|---|---|---|---|
| KGCGTRQCW | (109) | YRCREVLCQ | (110) | CWGTGLC | (111) |
| WSCADRTCM | (112) | AGCRLKSCA | (113) | SRCKTGLCQ | (114) |
| PICEVSRCW | (115) | WTCRASWCS | (116) | GRCLLMQCR | (117) |
| TECDMSRCM | (118) | ARCRVDPCV | (119) | CIEGVLGGC | (120) |
| CSVANSC | (121) | CSSTMRC | (122) | SIDSTTF | (123) |
| GPSRVGG | (124) | WWSGLEA | (125) | LGTDVRQ | (126) |
| LVGVRLL | (127) | GRPGDIW | (128) | TVWNPVG | (129) |
| GLLLVVP | (130) | FAATSAE | (131) | WCCRQFN | (132) |
| VGFGKAL | (133) | DSSLRLP | (134) | KLWCAMS | (135) |
| SLVSFLG | (136) | GSFAFLV | (137) | IASVRWA | (138) |
| TWGHLRA | (139) | QYREGLV | (140) | QSADRSV | (141) |
| YMFWTSR | (142) | LVRRWYL | (143) | TARGSSR | (144) |
| TTREKNL | (145) | PKWLLFS | (146) | LRTNVVH | (147) |
| AVMGLAA | (148) | VRNSLRN | (149) | | |

*numbers in parentheses indicate SEQ ID NO:.

Localization of the phage expressing a tumor homing peptide in the mouse organs also was examined by immunohistochemical staining of the tumor and various other tissues (see Example IV). In these experiments, $1 \times 10^9$ pfu of a control (insertless) phage or a phage expressing the tumor homing peptide, CLSGSLSC (SEQ ID NO: 4), were injected, iv, into tumor bearing mice and allowed to circulate for 4 min.

Immunostaining was evident in the melanoma obtained from a mouse injected with phage expressing the CLSGSLSC (SEQ ID NO: 4) tumor homing peptide. Staining of the melanoma generally was localized to the blood vessels within the tumor, although some staining also was present in the tumor parenchyma. Essentially no staining was observed in a tumor obtained from a mouse injected with the insertless control phage or in skin or in kidney samples obtained from mice injected with either phage. However, immunostaining was detected in the liver sinusoids and in spleen, indicating that phage can be trapped nonspecifically in organs containing RES.

Using similar methods, in vivo panning was performed in mice bearing a SLK human Kaposi's sarcoma. Tumor homing peptides were identified and are disclosed in Table 3. Together, these results demonstrate that the in vivo panning method is a generally applicable method for screening a phage library to identify phage expressing tumor homing peptides.

EXAMPLE VI

Preparation and Characterization of Tumor Homing Peptide/Doxorubicin Conjugates

This example provides methods for conjugating a moiety such as the chemotherapeutic agent, doxorubicin, to a tumor homing peptide and for characterizing the conjugation reaction.

The peptides CDCRGDCFC (SEQ ID NO: 1; Koivunen et al., supra, 1995; Pasqualini et al., supra, 1997), CNGRC (SEQ ID NO: 8), CGSLVRC (SEQ ID NO: 5) and GACVF-SIAHECGA (SEQ ID NO: 19) were synthesized, cyclized under high dilution and purified to homogeneity by HPLC. Conjugation of the peptides to doxorubicin (Aldrich; Milwaukee Wis.) was performed using 1-ethyl-3-(3-dimethylaminopropyl)carbodiimide hydrochloride (EDC; Sigma; St. Louis Mo.) and N-hydroxysuccinimide (NHS;

TABLE 3

PEPTIDES FROM PHAGE RECOVERED FROM HUMAN KAPOSI'S SARCOMA

| | | | | | |
|---|---|---|---|---|---|
| TDCTPSRCT | (150*) | SWCQFEKCL | (151) | VPCRFKQCW | (152) |
| CTAMRNTDC | (153) | CRESLKNC | (154) | CMEMGVKC | (155) |
| VTCRSLMCQ | (156) | CNNVGSYC | (157) | CGTRVDHC | (158) |
| CISLDRSC | (159) | CAMVSMED | (160) | CYLGVSNC | (161) |
| CYLVNVDC | (162) | CIRSAVSC | (163) | LVCLPPSCE | (164) |
| RHCFSQWCS | (165) | FYCPGVGCR | (166) | ISCAVDACL | (167) |
| EACEMAGCL | (168) | PRCESQLCP | (169) | RSCIKHQCP | (170) |
| QWCSRRWCT | (171) | MFCRMRSCD | (172) | GICKDLWCQ | (173) |
| NACESAICG | (174) | APCGLLACI | (175) | NRCRGVSCT | (176) |
| FPCEGKKCL | (177) | ADCRQKPCL | (178) | FGCVMASCR | (179) |
| AGCINGLCG | (180) | RSCAEPWCY | (181) | DTCRALRCN | (182) |
| KGCGTRQCW | (109) | GRCVDGGCT | (183) | YRCIARECE | (184) |
| KRCSSSLCA | (185) | ICLLAHCA | (186) | QACPMLLCM | (187) |
| LDCLSELCS | (188) | AGCRVESC | (189) | HTCLVALCA | (190) |
| IYCPGQECE | (191) | RLCSLYGCV | (192) | RKCEVPGCQ | (193) |
| EDCTSRFCS | (194) | LECVVDSCR | (195) | EICVDGLCV | (196) |
| RWCREKSCW | (197) | FRCLERVCT | (198) | RPCGDQACE | (199) |
| CNKTDGDEGVTC | (15) | | | | |

*numbers in parentheses indicate SEQ ID NO:.

Sigma) as described (Bauminger and Wilchek, supra, 1980; Harlow and Lane, supra, 1988; Hurwitz et al., supra, 1975). Unreacted doxorubicin and peptide were removed from the doxorubicin/peptide conjugates by SEPHADEX G25 column chromatography using phosphate buffered saline. The conjugates were lyophilized for storage and were resuspended in sterile water prior to use.

HPLC, capillary electrophoresis and NMR analyses were performed to characterize the conjugates. HPLC-fluorescence was performed using an INTERSIL ODS-2 column (4.6×150 mm) and a mobile phase composed of 0.08% triethanolamine/0.02% phosphoric acid (85%)/27% acetonitrile at 1 ml/min. Fluorescence detection was performed with excitation at 490 nm and emission at 560 nm wavelength and the retention time (RT) and the area under the curves (AUC) for doxorubicin (dox) and for the major peaks was determined. Each of the conjugates has a unique retention time, depending on the peptide, as follows: dox/CDCRGDCFC (SEQ ID NO: 1), RT 7.4 min, AUC 26%; dox/CNGRC (SEQ ID NO: 8), RT 4.7 min, AUC 56%; and dox/GACVFSIAHECGA (SEQ ID NO: 19), RT 7.7 min, AUC 43%. In comparison, the retention time of doxorubicin is 10.6 min and, in the various reactions, the AUC was about 5%.

Capillary electrophoresis (CE; Liu et al., supra, 1996) was performed in uncoated fused-silica capillaries with 75 μm internal diameter and an effective separation length of 50 cm. The CE detection system was equipped with an UV absorbance detector and an argon laser emitting at 488 nm. The laser beam is transmitted via a fiber optic cable to the detector and illuminates the capillary window and the fluorescence signal is collected through an emission filter. Conjugation of doxorubicin to the peptides changed the electrophoretic characteristics of each of the conjugates, indicating that this method can be used as a fast screening method to identify progress of the conjugation reaction.

One dimensional NMR analysis of the doxorubicin/CNGRC conjugate revealed no evidence of resonances arising from free doxorubicin. Two dimension NMR analysis can allow a determination of the precise molecular structure of the doxorubicin-peptide species.

These results demonstrate that a moiety such as the cancer chemotherapeutic agent, doxorubicin, can be efficiently linked to tumor homing peptides of the invention to produce doxorubicin/tumor homing peptide conjugates.

EXAMPLE VII

Tumor Therapy Using Doxorubicin/Tumor Homing Peptide Conjugates

This example demonstrates that doxorubicin/tumor homing peptide conjugates provide a therapeutic advantage over the use of doxorubicin, alone, for treating tumors.

Doxorubicin concentration. of the conjugates (see Example V) was determined by measuring the optical absorbance of the solution at 490 nm in a standard spectrophotometer; this wavelength detects only the doxorubicin, not the peptides. A calibration curve for doxorubicin was generated and used to calculate the concentration prior to use. Conjugation of doxorubicin to the various peptides did not affect this curve. This procedure ensures that each of the administered conjugates contained the same amounts of doxorubicin equivalent.

In addition, the viability of tumor cells obtained from tumors of mice treated with a tumor homing peptide/doxorubicin conjugate was compared to that of tumors from mice treated with free doxorubicin. In these experiments, breast tumor bearing mice were size matched with regard to the tumors, then treated intravenously with 30 μg equivalent of doxorubicin/CDCRGDCFC (SEQ ID NO: 1) or of free doxorubicin. Five days after treatment, the mice were euthanized and the tumors were removed. The tumor pairs were weighed and ground and the cell suspensions were plated (2 g tumor tissue per 150 mm plate).

Cell numbers were determined at 24 hours and 7 days after plating. Viability of tumor cells from the tumors of mice receiving the doxorubicin/CDCRGDCFC (SEQ ID NO: 1) conjugate was about 3 fold less than cells from tumors of mice treated with the free doxorubicin. These results demonstrate that administration to a tumor bearing mouse of a conjugate comprising a chemotherapeutic agent linked to a tumor homing molecule is more efficacious than administration of the agent, alone, in reducing the viability of tumor cells.

A. In vitro Characterization of Cytotoxicity

MDA-MB-435 human breast carcinoma cells were plated at 1×10$^5$ cells/well in 96 well plates. Cells were incubated with increasing amounts of doxorubicin, the doxorubicin/ CDCRGDCFC (SEQ ID NO: 1) conjugate, or the doxorubicin/GACVFSIAHECGA (SEQ ID NO: 19; control) conjugate (0.1 to 10 μg/well of doxorubicin-equivalent) for either 30 min or overnight. Following incubation, the agents were removed by extensive washing with PBS, then fresh medium added and incubation was continued. The number of surviving cells was determined at 24hours with crystal violet staining (see Koivunen et al., supra, 1994).

In cells exposed to free doxorubicin, the doxorubicin/ CDCRGDCFC (SEQ ID NO: 1) conjugate, or the doxorubicin/GACVFSIAHECGA (SEQ ID NO: 19) for 30 min, cell death was present only in the cultures treated with the doxorubicin/CDCRGDCFC (SEQ ID NO: 1) conjugate. However, if the agents were not removed after 30 min, the cells were killed by all of the treatments after 24 hr. These results indicate that enhanced cellular uptake occurs for the doxorubicin/CDCRGDCFC (SEQ ID NO: 1) conjugate.

B. In vivo Characterization of Doxorubicin/Tumor Homing Peptide Conjugates

Female 2-month old BALB/c nu/nu mice (Harlan Sprague Dawley; San Diego Calif.) were used for these studies and were cared for according to the Burnham Institute animal facility guidelines. MDA-MB-435 breast carcinoma cells (Price et al., *Cancer Res.* 50:717–721 (1993)) were injected in the mammary fat pad of the nude mice and tumor growth was monitored (Pasqualini et al., supra, 1997). Tumors were allowed to grow to a size of about 1 cm$^3$ (about 5% of the mouse's body weight) before starting the treatment experiments, except for the toxicity experiments as discussed below.

Weekly doxorubicin/peptide conjugate or control treatments (5 μg/mouse/week of doxorubicin-equivalent) were administered intravenously. In some experiments, as indicated, a dose of 30 μg/mouse was administered every 3 weeks. Treatment with doxorubicin, alone, is referred to as "dox control" and treatment with doxorubicin conjugated to the non-tumor homing control peptide, GACVFSIAHECGA (SEQ ID NO: 19), is referred to as "conjugate control." The results obtained in the dox control groups as compared to the conjugate control groups were not significantly different. As an additional control, in some experiments the tumor homing peptide was mixed with doxorubicin, without linking, and the mixture was administered to tumor bearing mice. Such treatment produced results that were not statistically different from those obtained with the above described dox controls.

Mice were anesthetized with a tribromoethanol-based anesthetic mixture (AVERTIN; Papaioannou and Fox, *Lab. Anim.* 43:189–192 (1993)) before each treatment. Anesthetization facilitated the tail vein injections (final volume, 200 μl) and allowed precise serial three dimensional tumor size measurements. Tumor volume calculations were based on the equation for the volume of an ovaloid: V=4/3 (Πabc), where a, b, and c are ½ of the measured diameters in each of the three dimensions.

At necropsy, MDA-MB-435 tumor-bearing mice treated with the doxorubicin/CDCRGDCFC (SEQ ID NO: 1) conjugate had significantly smaller tumors (t test, p=0.02), less spread to regional lymph nodes (t test, p<0.0001), a lower incidence of pulmonary metastasis and fewer metastatic lesions (t test, p<0.0001) than the dox control treated mice. All of the mice treated with the doxorubicin/CDCRGDCFC (SEQ ID NO: 1) conjugate survived beyond the time when the dox control and conjugate control mice had died (Log-Rank test, p<0.0001; Wilcoxon test, p=0.0007). Essentially the same results were obtained in five separate experiments. These results indicate that a doxorubicin/tumor homing peptide provides a therapeutic advantage over doxorubicin, alone, in reducing the growth of a primary tumor and preventing metastasis of the tumor.

Figure 2A:
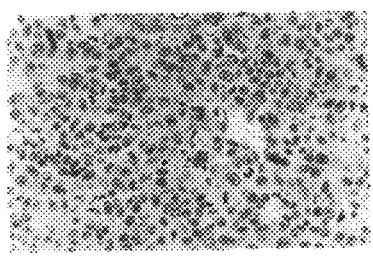
FIGS. 2A to 2F show the hematoxylin and eosin stained tumor samples from representative pairs of mice treated two times with 5 µg equivalent of doxorubicin (FIGS. 2A to 2C) or doxorubicin/CDCRGDCFC (SEQ ID NO: 1) conjugate (FIGS. 2D to 2F). Paired mice had size matched tumors at the time treatment was initiated.
Figure 2B:
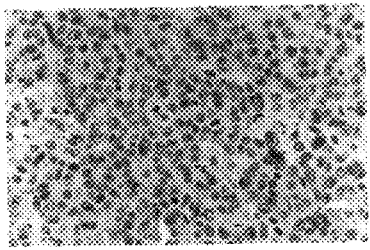
Figure 2C:
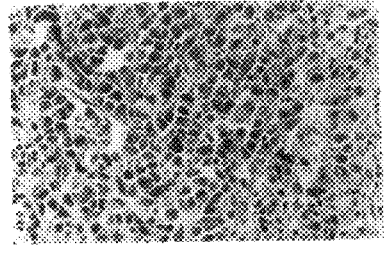
Figure 2D:
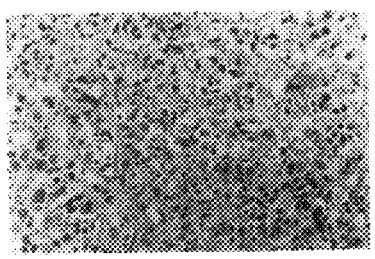
Figure 2E:
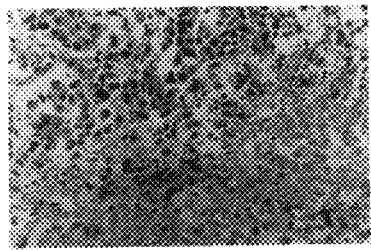
Figure 2F:
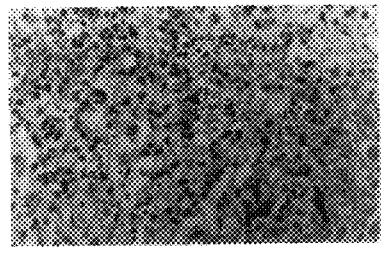

Gross and histopathologic examination was performed on the mice. Many of the. tumors in the mice treated with 5 μg doxorubicin equivalent of doxorubicin/CDCRGDCFC (SEQ ID NO: 1) presented marked skin ulceration and tumor necrosis, whereas no such signs were observed in dox control group or conjugate control group. Histopathological analysis disclosed a pronounced destruction of the vasculature in the tumors treated with doxorubicin/CDCRGDCFC (SEQ ID NO: 1) conjugate (see FIGS. 2D to 2F) as compared to the dox control group (FIGS. 2A to 2C).

In a dose escalation experiment, tumor bearing mice were treated with the doxorubicin/CDCRGDCFC (SEQ ID NO: 1) at 30 μg/mouse every three weeks for three cycles and were observed, without further treatment, for an extended period of time. The doxorubicin/CDCRGDCFC (SEQ ID NO: 1) treated mice all remained alive more than 6 months after the dox control and conjugate control mice had died. The results indicate that treatment with a doxorubicin/tumor homing peptide conjugate can have a curative effect.

Acute toxicity studies also were performed. In these experiments, mice bearing extremely large tumors (about 25% of body weight) were treated with 200 μg/mouse doxorubicin or doxorubicin/CDCRGDCFC (SEQ ID NO: 1) conjugate. All of the mice treated with the doxorubicin/ CDCRGDCFC (SEQ ID NO: 1) conjugate survived for longer than one week, whereas all of the dox control mice had died within 48 hr of treatment. These results suggest that accumulation of the doxorubicin/CDCRGDCFC (SEQ ID NO: 1) conjugate in the large tumors reduced the circulating level of the conjugated doxorubicin, thus reducing its toxicity.

Similar results were obtained using the doxorubicin/ CNGRC (SEQ ID NO: 8) conjugate. In each of three series of experiments, tumors in the mice treated with doxorubicin/ CNGRC (SEQ ID NO: 8) were significantly smaller than tumor is the dox control and conjugate control groups. Treatment with the:doxorubicin/CNGRC (SEQ ID NO: 8) conjugate almost completely suppressed tumor growth, whereas free doxorubicin and doxorubicin conjugated to the control peptide had essentially no effect on tumor growth relative to treatment with the vehicle, alone. A marked effect on survival also was observed and some of the doxorubicin/ CNGRC (SEQ ID NO: 8) treated animals survived for extended periods of time (Log-Rank test, p=0.0064; Wilcoxon test, p=0.0343). In addition, the doxorubicin/CNGRC (SEQ ID NO: 8) conjugate was less toxic than free doxorubicin. These results confirm that conjugates comprising a chemotherapeutic agent and a tumor homing molecule provide a therapeutic advantage in treating cancer.

Although the invention has been described with reference to the disclosed examples, it should be understood that various modifications can be made without departing from the spirit of the invention. Accordingly, the invention is limited only by the following claims.

---

We claim:

1. A conjugate, comprising a peptide comprising the amino acid sequence NGR, said peptide linked to a therapeutic moiety selected from the group consisting of a cytotoxic agent and a cancer chemotherapeutic agent,
   wherein said conjugate selectively homes to angiogenic vasculature upon in vivo administration.

2. A conjugate, comprising a peptide comprising the amino acid sequence NGR, said peptide linked to a cytotoxic agent, wherein said conjugate selectively homes to angiogenic vasculature upon in vivo administration.

3. A conjugate, comprising a peptide comprising the amino acid sequence NGR, said peptide linked to a cancer chemotherapeutic agent, wherein said conjugate selectively homes to angiogenic vasculature upon in vivo administration.

4. The conjugate of claim 3, wherein said cancer chemotherapeutic agent is doxorubicin.

5. The conjugate of claim 1, wherein said peptide comprises the amino acid sequence NGRAHA (SEQ ID NO: 6).

6. The conjugate of claim 5, wherein said therapeutic moiety is doxorubicin.

7. The conjugate of claim 1, wherein said peptide. comprises the amino acid sequence CNGRC (SEQ ID NO: 8).

8. The conjugate of claim 7, wherein said therapeutic moiety is a cancer chemotherapeutic agent.

9. The conjugate of claim 8, wherein said cancer chemotherapeutic agent is doxorubicin.

10. The conjugate of claim 1, wherein said peptide comprises the amino acid sequence CNGRCVSGCAGRC (SEQ ID NO: 3).

11. The conjugate of claim 10, wherein said therapeutic moiety is a cancer chemotherapeutic agent.

12. The conjugate of claim 11, wherein said cancer chemotherapeutic agent is doxorubicin.

13. The conjugate of claim 1, wherein said peptide has a length of up to thirty amino acids.

14. The conjugate of claim 1, wherein said peptide has a length of up to twenty amino acids.

15. The conjugate of claim 1, wherein said peptide is 50 to 100 amino acids in length.

16. A conjugate, comprising a peptide consisting of the amino acid sequence NGRAHA (SEQ ID NO: 6), said peptide linked to a therapeutic moiety selected from the group consisting of a cytotoxic agent and a cancer chemotherapeutic agent, wherein said conjugate selectively homes to angiogenic vasculature upon in vivo administration.

17. A conjugate, comprising a peptide consisting of the amino acid sequence CNGRC (SEQ ID NO: 8), said peptide linked to a therapeutic moiety selected from the group consisting of a cytotoxic agent and a cancer chemotherapeutic agent, wherein said conjugate selectively homes to angiogenic vasculature upon in vivo administration.

18. A conjugate, comprising a peptide consisting of the amino acid sequence CNGRCVSGCAGRC (SEQ ID NO: 3), said peptide linked to a therapeutic moiety selected from the group consisting of a cytotoxic agent and a cancer chemotherapeutic agent.

19. A peptide, comprising the amino acid sequence CNGRCVSGCAGRC (SEQ ID NO: 3).

20. The peptide of claim 19, which has a length of up to thirty amino acids.

21. The peptide of claim 20, which has a length of up to twenty amino acids.

22. The peptide of claim 19, which has a length of 50 to 100 amino acids.

23. The peptide of claim 19, consisting of the amino acid sequence CNGRCVSGCAGRC (SEQ ID NO: 3).

24. A conjugate, comprising a peptide comprising the amino acid sequence NGR, said peptide linked to a phage, wherein said conjugate selectively homes to angiogenic vasculature upon in vivo administration.

25. A conjugate, comprising a peptide comprising the amino acid sequence NGRAHA (SEQ ID NO: 6), said peptide linked to a phage, wherein said conjugate selectively homes to angiogenic vasculature upon in vivo administration.

26. A conjugate, comprising a peptide comprising the amino acid sequence CNGRC (SE Q ID NO: 8), said peptide linked to a phage, wherein said conjugate selectively homes to angiogenic vasculature upon in vivo administration.

27. A conjugate, comprising a peptide comprising the amino acid sequence CNGRCVSGCAGRC (SEQ ID NO: 3), said peptide linked to a phage, wherein said conjugate selectively homes to angiogenic vasculature upon in vivo administration.

28. The conjugate of claim 2, wherein said peptide comprises the amino acid sequence NGRAHA (SEQ ID NO: 6).

29. The conjugate of claim 3, wherein said peptide comprises the amino acid sequence NGRAHA (SEQ ID NO: 6).

30. The conjugate of claim 2, wherein said peptide comprises the amino acid sequence CNGRC (SEQ ID NO: 8).

31. The conjugate of claim 3, wherein said peptide comprises the amino acid sequence CNGRC (SEQ ID NO: 8).

32. The conjugate of claim 2, wherein said peptide comprises the amino acid sequence CNGRCVSGCAGRC (SEQ ID NO: 3).

33. The conjugate of claim 3, wherein said peptide comprises the amino acid sequence CNGRCVSGCAGRC (SEQ ID NO: 3).

* * * * *